US010940332B2

United States Patent
Zhang et al.

(10) Patent No.: US 10,940,332 B2
(45) Date of Patent: Mar. 9, 2021

(54) CHERENKOV IMAGING SYSTEMS AND METHODS TO MONITOR BEAM PROFILES AND RADIATION DOSE WHILE AVOIDING INTERFERENCE FROM ROOM LIGHTING

(71) Applicant: THE TRUSTEES OF DARTMOUTH COLLEGE, Hanover, NH (US)

(72) Inventors: Rongxiao Zhang, Norwich, VT (US); Brian William Pogue, Hanover, NH (US); Adam K. Glaser, Lebanon, NH (US); David J. Gladstone, Norwich, VT (US); Lesley A. Jarvis, Hanover, NH (US); Jacqueline M. Andreozzi, West Lebanon, NH (US); Shudong Jiang, Hanover, NH (US); Scott Christian Davis, Woodsville, NH (US); Johan Jakob Axelsson, Lund (SE)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 1134 days.

(21) Appl. No.: 15/160,576

(22) Filed: May 20, 2016

(65) Prior Publication Data

US 2016/0263402 A1 Sep. 15, 2016

Related U.S. Application Data

(63) Continuation-in-part of application No. PCT/US2016/029458, filed on Apr. 27, 2016, and a
(Continued)

(51) Int. Cl.
*A61B 5/05* (2006.01)
*A61B 5/00* (2006.01)
*A61N 5/10* (2006.01)

(52) U.S. Cl.
CPC ......... *A61N 5/1071* (2013.01); *A61N 5/1049* (2013.01); *A61N 5/1077* (2013.01);
(Continued)

(58) Field of Classification Search
None
See application file for complete search history.

(56) References Cited

U.S. PATENT DOCUMENTS

| 4,215,274 A | 7/1980 | Segall |
| 5,117,829 A | 6/1992 | Miller et al. |

(Continued)

FOREIGN PATENT DOCUMENTS

| GB | 681050 | 10/1952 |
| WO | WO 2011/005862 | 1/2011 |

(Continued)

OTHER PUBLICATIONS

"Cho et sl.," "Cerenkov radiation imaging as a method for quantitative measurements of beta particles in a microfluidic chip," Phys Med Biol. Nov. 21, 2009; 54 (22):6757-6771.*
(Continued)

*Primary Examiner* — Patricia J Park
(74) *Attorney, Agent, or Firm* — Lathrop GPM LLP

(57) ABSTRACT

A monitor for pulsed high energy radiation therapy using a radiation beam passing through a treatment zone, the radiation of 0.2 MEV or greater; has a camera for imaging Cherenkov light from the treatment zone; apparatus for preventing interference by room lighting, the camera synchronized to pulses of the radiation beam; and an image processor adapted to determine extent of the beam area on the patient skin from the images. Additionally an image processor determines cumulative skin dose in the treatment zone from the images. In embodiments, the processor uses a three-dimensional model of a subject to determine map-
(Continued)

ping of image intensity in images of Cherenkov light to radiation intensity in skin, applies the mapping to images of Cherenkov light to verify skin dose delivered, and accumulates skin dose by summing the maps of skin dose.

24 Claims, 13 Drawing Sheets

Related U.S. Application Data continuation-in-part of application No. PCT/US2014/066668, filed on Nov. 20, 2014, and a continuation-in-part of application No. 14/118,825, filed as application No. PCT/US2012/038609 on May 18, 2012, now Pat. No. 10,201,718.

(60) Provisional application No. 62/153,417, filed on Apr. 27, 2015, provisional application No. 61/906,805, filed on Nov. 20, 2013, provisional application No. 61/585,366, filed on Jan. 11, 2012, provisional application No. 61/488,129, filed on May 19, 2011.

(52) U.S. Cl.
CPC .... *A61N 5/1065* (2013.01); *A61N 2005/1054* (2013.01); *A61N 2005/1059* (2013.01)

(56) References Cited

U.S. PATENT DOCUMENTS

| | | | |
|---|---|---|---|
| 6,123,719 | A | 9/2000 | Masychev |
| 6,518,580 | B1* | 2/2003 | van Bibber ............... G01T 1/22 250/397 |
| 6,552,347 | B1 | 4/2003 | Dimcovski |
| 2003/0143637 | A1 | 7/2003 | Selvan |
| 2003/0225325 | A1 | 12/2003 | Kagermeier et al. |
| 2006/0215885 | A1 | 9/2006 | Kates |
| 2006/0285639 | A1 | 12/2006 | Olivera |
| 2007/0164225 | A1* | 7/2007 | Pang .......................... G01T 1/22 250/367 |
| 2009/0018415 | A1 | 1/2009 | Robinson |
| 2010/0119032 | A1 | 5/2010 | Yan et al. |
| 2010/0145416 | A1 | 6/2010 | Kang et al. |
| 2010/0254568 | A1 | 10/2010 | Fanenbruck |
| 2010/0265316 | A1* | 10/2010 | Sali ...................... H04N 13/254 348/46 |
| 2010/0330545 | A1 | 12/2010 | Tian |
| 2010/0331927 | A1 | 12/2010 | Cottrell et al. |
| 2011/0001049 | A1 | 1/2011 | Shibuya |
| 2011/0117025 | A1 | 5/2011 | Dacosta |
| 2011/0163236 | A1 | 7/2011 | Arodzero |
| 2011/0248188 | A1* | 10/2011 | Brusasco ............. A61N 5/1048 250/492.1 |
| 2012/0220870 | A1 | 8/2012 | Gambhir |
| 2012/0276002 | A1 | 11/2012 | Yoo |
| 2013/0044185 | A1 | 2/2013 | Krishnaswamy et al. |
| 2013/0108132 | A1 | 5/2013 | Klose |
| 2013/0188856 | A1 | 7/2013 | Adler, Jr. et al. |
| 2013/0259339 | A1* | 10/2013 | Tian ......................... G01T 1/22 382/131 |
| 2014/0064554 | A1 | 3/2014 | Coulter et al. |
| 2014/0114150 | A1 | 4/2014 | Pogue et al. |

FOREIGN PATENT DOCUMENTS

| | | |
|---|---|---|
| WO | WO 2012/159043 | 11/2012 |
| WO | WO 2014/020360 | 2/2014 |

OTHER PUBLICATIONS

European Patent Application No. 16787023.7; Extended European Search Report and Opinion dated Feb. 22, 2019—8 pgs.
Cho et al.,"Cerenkov radiation imaging as a method for quantitative measurements of beta particles in a microfluidic chip," Phys Med Biol., Nov. 21, 2009; 54 (22), 22 pp.
Non-Final Rejection mailed in U.S. Appl. No. 14/118,825 dated Jan. 19, 2018, 26 pages.
Final Rejection mailed in U.S. Appl. No. 14/118,825 dated Aug. 23, 2017, 26 pages.
U.S. Appl. No. 14/118,825; Office Action dated Jan. 13, 2017; 23 pgs.
International Search Report and Written Opinion in PCT/US2016/029458 dated Jul. 27, 2016, 12 pp.
Fodor et al., Aesthetic Applications of Intense Pulsed Light, Springer-Verlag London Limited, 2011, 148 pp.
Jarvis et al "Cherenkov Video Imaging Allows for the First Visualization of Radiation Therapy 1-29 in Real Time", International Journal of Radiation Oncology, Jan. 27, 2014, 8 pp.
PCT Patent Application PCT/US2014/066668 International Search Report and Written Opinion dated Feb. 24, 2015, 11 pages.
PCT Patent Application PCT/US12/38609 International Search Report and Written Opinion dated Dec. 3, 2012, 11 pages.
U.S. Appl. No. 14/118,825, Final Office Action dated Jul. 27, 2016, 25 pp.
U.S. Appl. No. 14/118,825, Non-Final Office Action dated Jan. 12, 2016, 21 pp.

\* cited by examiner

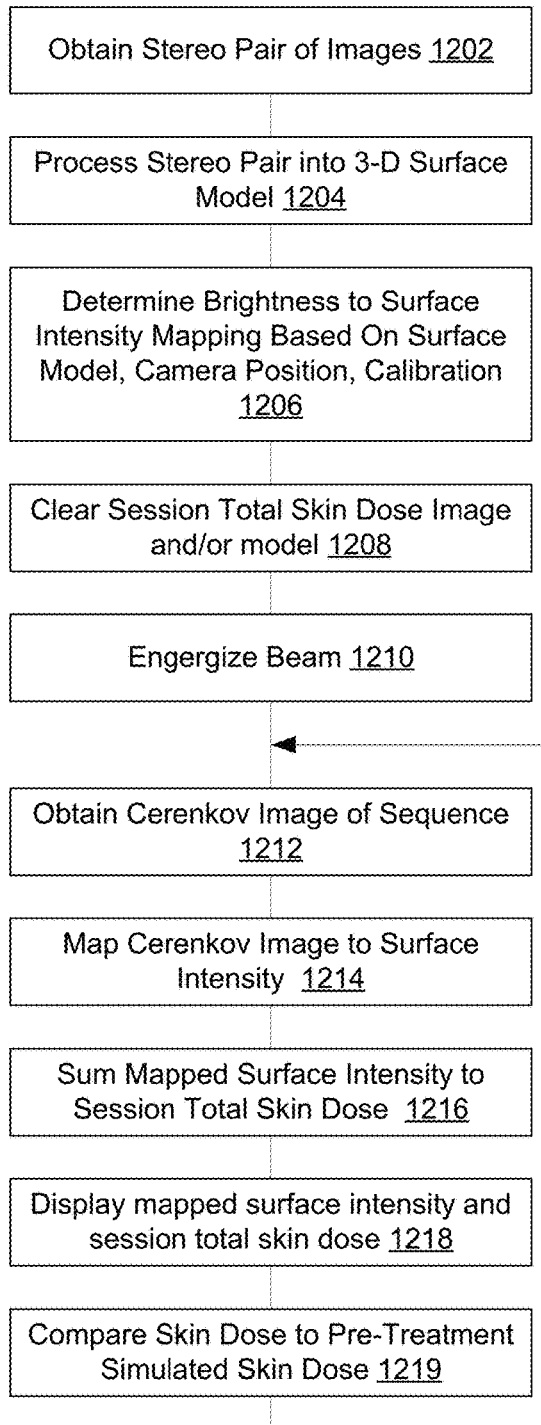
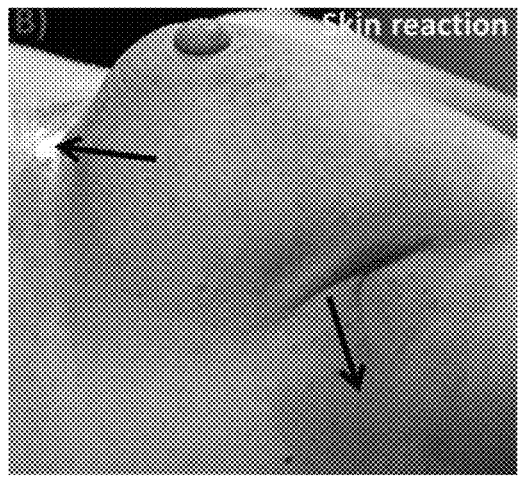
FIG. 17
FIG. 15 ium is reduced relative to air or vacuum due to its refractive index being greater than unity. Therefore fast-moving charged particles release Cherenkov radiation after entering such tissue. Water is also a medium where the speed of light is reduced relative to air or vacuum, fast-moving charged particles in water also release Cherenkov radiation after entering such water. Cherenkov emission has been detected with incident radiation in the range of 6 to 24 MeV energies for both x-ray photons as well as electrons. It is expected that Cherenkov radiation will also be released from beams of very-high-energy protons and other charged particles.

CHERENKOV IMAGING SYSTEMS AND METHODS TO MONITOR BEAM PROFILES AND RADIATION DOSE WHILE AVOIDING INTERFERENCE FROM ROOM LIGHTING

RELATED APPLICATIONS

This application is a continuation-in-part of PCT/US16/29458, filed Apr. 27, 2016, which claims priority to U.S. Provisional Patent Application No. 62/153,417 filed Apr. 27, 2015. This application is also a continuation-in-part of International Application No. PCT/US14/66668, filed Nov. 20, 2014, which claims priority to U.S. Provisional Patent Application 61/906,805, filed Nov. 20, 2013, and this application is a continuation-in-part of U.S. patent application Ser. No. 14/118,825, with a filing date of May 18, 2012 and § 371(c) date of Nov. 19, 2013, which is a § 371 National Phase Application of PCT Patent Application Serial No. PCT/US12/38609 filed May 18, 2012, which claims priority to U.S. Provisional Patent Application 61/488,129, filed May 19, 2011 and to U.S. Provisional Patent Application 61/585,366, filed Jan. 11, 2012. The disclosures of all these prior applications are incorporated herein by reference in their entireties.

GOVERNMENT INTEREST

This invention was made with Government support under NIH Grant Nos. R01CA109558 and R21EB017559, both awarded by the National Institutes of Health. The Government has certain rights to the inventions.

FIELD

The present document describes apparatus and methods for imaging and monitoring radiation treatments such as are frequently administered in malignant diseases.

A portion of the material disclosed herein resembles that in the published paper article entitled Cherenkov Video Imaging allows for the first visualization of radiation therapy in real time by Lesley A Jarvis, Rongxiao Zhang, David J. Gladstone, Shudong Jiang, Whitney Hitchcock, Oscar D. Friedman, Adam K. Glaser, Michael Jermyn, and Brian W. Pogue, reported in the International Journal of Radiation Oncology, Biology and Physics Volume 89, Issue 3, pp. 615-622, on Jul. 1, 2014 (Epub Mar. 28, 2014). The entire contents of this article are incorporated herein by reference.

This document relates to the detection and use of Cherenkov radiation (sometimes spelled Cerenkov radiation or Cerenkov radiation) emitted as a radiation beam strikes tissue to observe, verify accuracy in delivery and then also potentially control radiation treatment machines, to ensure that medical radiation prescription protocols are properly followed

BACKGROUND

It is desirable when treating cancers with radiation to have a high ratio of energy deposited in the tumor, relative to energy deposited in normal tissues surrounding the tumor, resulting in a high therapeutic ratio of tumor to normal dose. Radiation treatments using high energy electron particle beams or high energy photon beams are used in the treatment of many cancers. Such beams are typically provided by a linear accelerator, a cyclotron, or related apparatus.

Charged particles, such us electrons, positrons, protons, or alpha particles, moving at greater than the effective speed of light in a medium tend to slow down while releasing Cherenkov radiation. Mammalian tissue, including human tissue, is a med When this Cherenkov light is induced in tissue, it is predominantly blue in color, but with a broad spectrum which tapers off into the green, red, and near-infrared (NIR) with an inverse square wavelength dependence given by the Frank-Tamm formula. This light emitted in tissue is attenuated by absorbers in the tissue, and can also excite other molecular species in tissue, inducing their photo-luminescence (fluorescence or phosphorescence).

Prior to treating patients with high energy beams, it is desirable to know the shape of the beam, and to verify that the beam shape is as planned. Additionally, when beams enter tissue it is important to accurately predict how radiation beam shape varies with depth in tissue, to ensure adequate dosage to tumor while minimizing dosage to surrounding normal tissues. If beam shape and position is adjusted by positioning deflection magnets or shielding devices, it can be important to confirm that the resulting beam shape and dosage profile are as desired prior to exposing patients to the beam; radiation treatment centers may therefore desire to confirm beam shape and dose profile for complex beam shaping procedures for each patient, or as part of routine calibration and maintenance.

Manufacturers of radiation treatment devices often prepare documentation of beam shapes and dosage profiles produced by common configurations of their devices for training users and guiding operators in using their machines to treat patients. Further, they must seek regulatory approvals of their machines, and as part of the regulatory approvals process they are expected to provide documentation of beam shapes and dosage profiles achievable by their machines. Manufacturers may therefore also need to accurately verify and document beam profiles for this regulatory approval process.

It is also desirable to monitor treatment in real-time, both to ensure treatment protocols are met and prevent accidental overdosing, and to image an intersection of the beam with skin to ensure that beam profiles are as expected for treatment protocols.

SUMMARY

In an embodiment, a system for providing monitored radiation therapy has a source of pulsed high energy radiation disposed to provide a radiation beam to a treatment zone, the high energy radiation of 200 keV or greater; a camera for imaging Cherenkov light from the treatment zone; apparatus for preventing interference by room lighting by synchronizing the camera to pulses of the radiation beam and blanking room lighting during pulses of radiation; and an image processor adapted to determine cumulative skin dose in the treatment zone from the images.

In an alternative embodiment, a system for providing and monitoring delivery and accuracy of radiation therapy has a source of pulsed high energy radiation disposed to provide a radiation beam to a treatment zone, at least one imaging system camera configured to obtain observations images of light emitted from the treatment zone, the camera is synchronized to pulses of the pulsed high energy radiation. The system also has an image processor.

In a particular embodiment, the image processor has firmware adapted to subtract images acquired when the pulsed high energy radiation is off from images acquired when the pulsed high energy radiation is on to generate images of Cherenkov light.

In a particular embodiment, the processor uses a three-dimensional model of a subject to determine a mapping of image intensity in the images of Cherenkov light to radiation intensity in skin of the subject, to acquire multiple images of Cherenkov light, to apply the mapping to the images of Cherenkov light to map skin dose, and to accumulate skin dose by summing the maps of skin dose.

In another particular embodiment, biological features apparent in the tissue which appear in the Cherenkov emission image can be used as landmarks or fiducials for verification of the beam delivery accuracy. In particular the major blood vessels have high Cherenkov absorption and appear as dark lines in the image, and are therefore apparent in the images and useful for soft tissue fiducials. These are apparent in successive days in fractionated therapy, so that they could be used for patient alignment verification on a day to day basis. The images can be recorded and saved in the patient record for a permanent verification of the delivered radiation treatment.

In another embodiment, a method of determining surface dose during radiation treatment of a first object beneath a surface of a second object to limit dose at the surface includes obtaining stereo images of the surface, and extracting a three-dimensional computer model of the surface; determining a mapping of image brightness at the surface in Cherenkov light images obtained by a digital camera to radiation intensity; recording surface brightness at the surface in a plurality of Cherenkov light images; and a summing step including using the mapping of image brightness at the surface to translate each Cherenkov light image into a surface dose image, or summing the surface dose images to provide a total session surface dose image. The method continues with summing the image brightness in each Cherenkov light image into a total session surface Cherenkov light image and using the mapping of image brightness at the surface to translate the total session surface Cherenkov light image into a total session surface dose image. The method concludes with displaying the total session surface dose image.

In an embodiment, a Cherenkov imaging system for determining surface radiation dose for a subject undergoing radiation therapy includes (a) a first camera for capturing a Cherenkov image of Cherenkov radiation from a surface region of the subject undergoing Cherenkov-radiation-inducing radiation therapy, (b) a second camera for capturing a reflectance image of reflectance of optical illumination off the surface region, and (c) a correction module for correcting the Cherenkov image based upon the reflectance image to form a corrected Cherenkov image that indicates radiation dose for the surface region.

In an embodiment, a Cherenkov imaging method for determining surface radiation dose for a subject undergoing radiation therapy includes correcting a Cherenkov image, of Cherenkov radiation from a surface region of the subject undergoing Cherenkov-radiation-inducing radiation therapy, using a reflectance image, of optical illumination reflected by the surface region, to form a corrected Cherenkov image that indicates radiation dose for the surface region.

BRIEF DESCRIPTION OF THE DRAWINGS

FIG. 15 is a flowchart of operation of the system of FIG. 13

FIG. 17 is a photograph of a subject indicating areas of skin damage correlated to areas of high dose in FIG. 16.

DETAILED DESCRIPTION OF THE EMBODIMENTS

Figure 1:
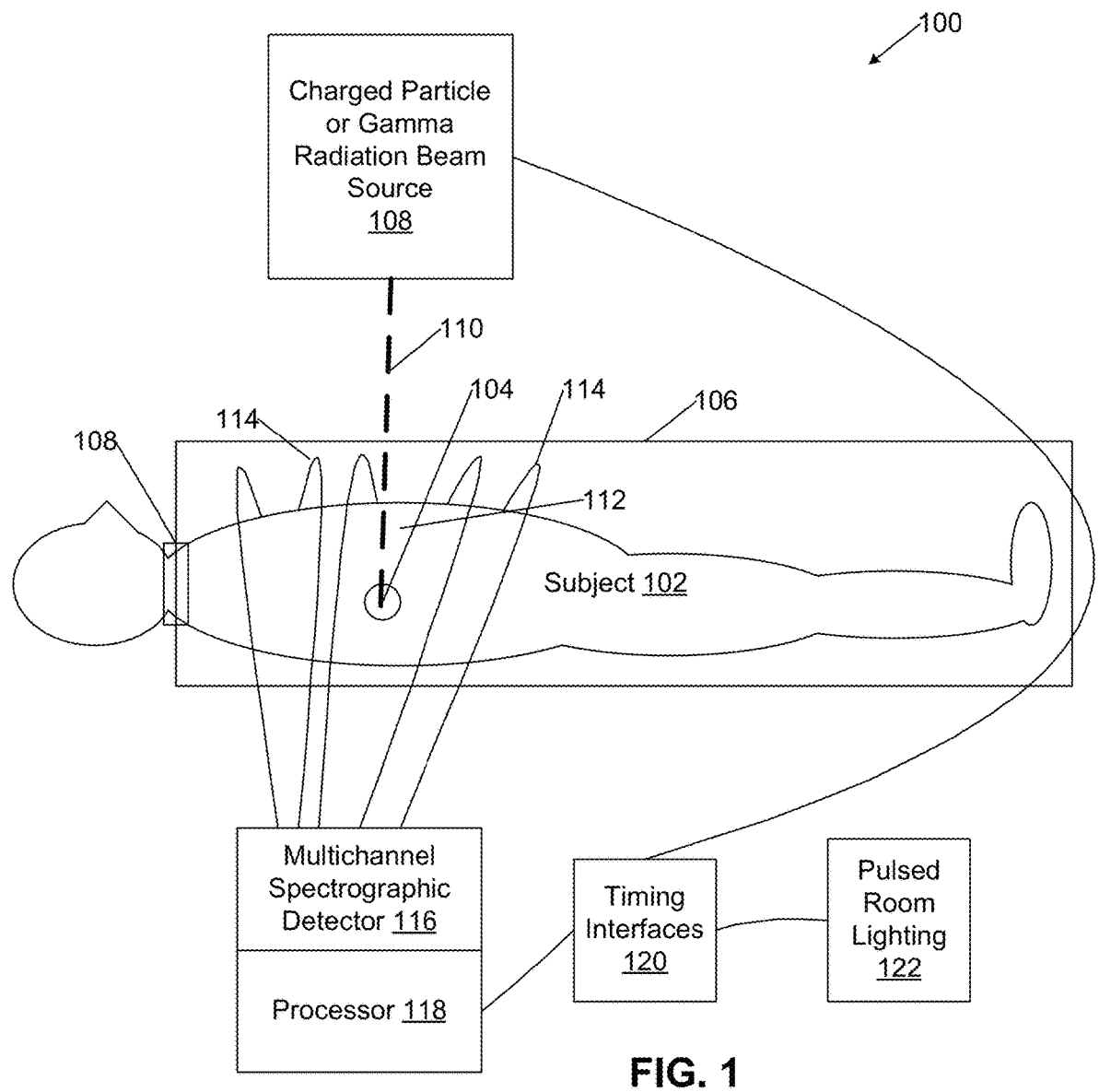
FIG. 1 is an illustration of a system for performing monitored radiotherapy.

A system 100 for providing radiotherapy and monitoring factors known to affect the effectiveness of radiotherapy, and monitoring effects of radiotherapy on tissue, is illustrated in FIG. 1.

Portions of a subject 102 containing a tumor 104 requiring radiotherapy are placed within an enclosure 106 for excluding light. The enclosure 106 may be made of black plastic or cloth, and has a sealing portion 108 drawn tight by an elastomeric band such that a subject's eyes may be permitted access to ambient light and thereby prevent claustrophobia while still excluding room light from optical fibers 114. It is anticipated that a variety of enclosures 106 may be provided to exclude light from various portions of a subject in various embodiments, in some embodiments light may be excluded from a subject's cranium, in others from a subject's chest or abdomen, according to location of tumor 104 within subject 102 and desired beam angles.

In an alternative embodiment, enclosure 106 is an entire room containing the subject 102. In order to improve subject comfort, and taking advantage of visual persistence of the human eye and the pulsed nature of many radiation sources such as linear and cyclotron accelerators, a rapidly pulsed light source 107 is used that appears steady to the human eye. Pulses of light source 107 are timed, and appropriate gating of the detector 116 or camera 117 used, such that imaging or sensing of Cherenkov radiation is done at intervals where light source 107 is off, and radiation beam 110 is on. Acquisition of Cherenkov images is thereby done in synchronized room light conditions.

An accelerator 108, or other device for providing high energy radiation, is aimed to provide a beam 110 of radiation through normal tissue 112 to tumor 104. In all embodiments, the system herein described uses incident radiation from accelerator 108 at beam energies of at least 200 keV because, at beam energies of less than 200 keV (0.2 MeV), Cherenkov radiation is typically of insufficient intensity for imaging. In a particular embodiment, the accelerator 108 provides a beam of electrons having energy of 6 million electron volts (6 MeV) or greater, in a particular embodiment the beam energy lies between 6 and 24 MeV. In an alternative embodiment, the device for providing high energy radiation provides a beam of high energy photons, the photons interact with tissue or tumor to produce charged particles that in turn produce Cherenkov radiation. In an alternative embodiment, the accelerator 108 provides a high-energy proton beam. In an alternative embodiment, the radiation source is implanted in the body, inducing Cherenkov emission light directly as charged particles are emitted during radiation decay. The subject 102 and enclosure 106 is positioned within a room having subdued lighting.

Since high radiation doses are desired in tumors, while high doses are not desired in surrounding normal tissue or on skin because those tissues can be damaged by radiation, provisions are typically made for varying arriving beam delivery angles by, for example, rotating the subject and enclosure in the beam, rotating the radiation source about the subject and enclosure, or periodically interrupting treatment to reposition the subject and enclosure. Additionally the beam is shaped either in a static beam, or in other embodiments the beam shape is dynamically changed while rotation is performed, to allow customized dose delivery to the shape of the tumor to be treated, at each delivered beam angles.

At least one, and in an embodiment an array of many, optical fibers 114 are provided and positioned, such as in contact with or close to, subject 102 in enclosure 106, for collecting any light that may be emitted from subject 102. In an alternative embodiment, a camera system 117, having a lens system adapted to collecting light from the subject and an array photosensor for detecting the collected light, positioned some distance from the subject is used to image light emitted from the tissue.

Optical fibers 114 provide light to multichannel spectrographic detector 116. For each channel of the multichannel spectrographic detector 116 there is a wavelength-dependent dispersive device such as a prism or diffraction grating for separating light according to wavelength, and an array of photosensors such as a CCD or CMOS sensor, an array of PIN diodes, or an array of photomultiplier tubes. In another embodiment, optical filters are inserted in the detection channel before the spectrograph to reduce ambient light and Cherenkov emission above or below a specified wavelength range, thus reducing the required dynamic range of the detector.

For convenience in this document, the array of optical fibers 114 and detector 116, or camera 117, are forms of an imaging system adapted to imaging light from subject 102, such as Cherenkov light generated by interactions of the beam of high energy radiation with tissue of the subject.

Detector 116 provides information indicative of received light amplitude at each of many wavelengths to processor 118. Processor 118 analyzes this information to provide indications of heme concentration in tumor, oxygen concentration in tumor, and other parameters (such as metabolic activity and oxygenation) provided by photo-luminescent emission In an alternative embodiment, detector 116 is a spectrally sensitive detector constructed of a filter wheel and photodetector, providing spectral information on captured light from fiber 114 by alternately interposing an assortment of filters each having a passband at a wavelength of interest. In an alternative embodiment, a tunable filter is used in place of a filter wheel. In another alternative embodiment, a filter wheel or tunable filter is placed in front of a camera positioned some distance from the subject. This embodiment allows collection of a series of images, each image of the series imaging light from the subject at a different wavelength band, to allow spectral analysis on the series of images.

In an alternative embodiment, detector 116 is timed to be enabled in a temporal relationship after each radiation pulse, such that the emissions from Cerenkov excited luminescence, such as phosphorescence or fluorescence, are captured, allowing a capture of images of light emitted from a secondarily-emitting chemical or indicating agent, such as a fluorescent or phosphorescent chemical, in or on the tissue and as stimulated by Cherenkov radiation emitted as radiation interacts with the tissue. This time sequenced signal is generated from the Cherenkov radiation, but can provide information regarding the bio-molecular environment of the tissue being irradiated. The secondarily-emitting chemical in some embodiments is a chemical intrinsic to the body, and in some embodiments is a drug, or a metabolite of a prodrug, that is administered to the subject.

In an alternative embodiment, detector 116 is replaced with a camera 117 having similar timing characteristics and spectral sensitivity. The imager, whether including detector 116 and/or camera 117, in embodiments using secondarily-emitting substances may be sensitive to light in infrared as well as some visible wavelengths.

In a particular embodiment, the imager is a hyperspectral camera. For purposes of this document, a hyperspectral camera is a camera having spectral response that extends beyond the visible light spectrum, such as a camera able to respond to at least some near-infrared light. Further, a hyperspectral camera is a camera that is adapted to resolve wavelengths of received light into more, and narrower, bins than the three (red, green, and blue) wavelength bins of a typical color electronic camera. Hyperspectral cameras are known in the electronic camera art that are capable of resolving received light into dozens of wavelength bands, including one or more infrared bands; such cameras may operate by using patterned filters on photosensor arrays that have more than the usual three colors of filters, or by using line-scanning spectrographic techniques.

Figure 2:
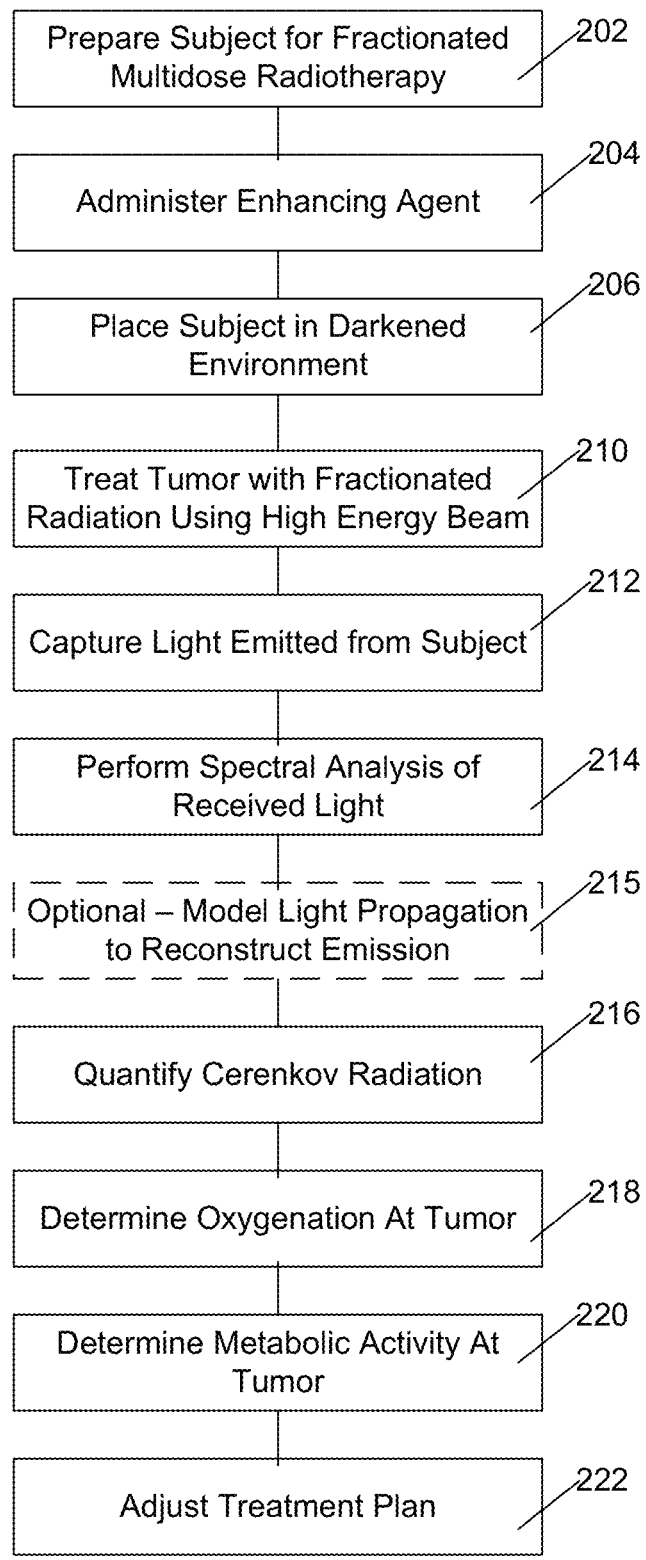
FIG. 2 is an approximate flowchart of a method of monitoring radiotherapy.

The system 100 is operated according to a method illustrated in FIG. 2. The subject is prepared 202 for multidose radiotherapy as known in the art of radiotherapy; tumor 104 is localized and imaged, alignment marks may be applied by tattoo or in other ways, and aiming and positioning masks or frames may be made. A desired dose of radiation for each session is prescribed.

Prior to each session for which monitoring is desired, in an embodiment an enhancing and indicating agent is administered 204. In an embodiment, the enhancing and indicating agent is a dose of 20 milligrams per kilogram body weight of 5-delta-aminolevulinic acid (5-ALA), the dose being administered an incubation time of approximately four hours before each divided radiotherapy session begins.

In metabolically active tumor 104, some of the 5-ALA is metabolized to Protoporphyrin IX (PpIX). In alternative embodiments, it is expected that other enhancing agents may be developed or utilized. PpIX production in normal tissue 112 and tumor 104 is due to metabolic processes in those tissues and a quantity of PpIX produced in those tissues is dependent on an amount of metabolic activity in those tissues.

The subject 102 is then placed 206 in a darkened environment, which in an embodiment includes placing those parts of the subject to be subjected to radiotherapy within enclosure 106, and positioning light collecting fibers 114 to collect light from the subject 102, as heretofore described with reference to the enclosure.

The tumor is then treated 210 by having accelerator 108 then provide a beam of high energy charged particles aimed along a beam path at tumor 104 to perform radiotherapy of the tumor. In an embodiment, the subject 102 may be rotated during the session to distribute radiation absorbed by normal tissues 112 while maintaining beam targeting at tumor 104.

As charged particles of beam 110 decelerate in both normal tissue 112 and tumor 104, these particles generate light by Cherenkov radiation, with broadband spectral constituents decreasing with wavelength to the inverse square power.

Some of the light generated by Cherenkov radiation propagates to light collecting fibers 114, and some may be absorbed by fluorophores (or phosphors) within subject 102, including fluorophores (or phosphors) within normal tissue 112 and tumor 104. Among fluorophores within subject 102 are any PpIX produced from metabolic activity in tissue 112 and tumor 104. Light from Cherenkov radiation that is absorbed by fluorophores (or phosphors) in tissue and tumor may stimulate photo-luminescent emission by those tissues and tumor.

Light from both Cherenkov radiation and photo-luminescent emission propagates from the beam path to a surface of the subject 102, intersecting any tissue between the tumor and the surface, and being attenuated by absorption from molecular absorbers such as deoxyhemoglobin, oxyhemoglobin, proteins, lipids and water before being emitted from the subject.

The dominant absorption is from deoxyhemoglobin and oxyhemoglobin, which differ in their spectral absorption, and so changes in spectral characteristics of the attenuated light emitted from the subject are a reasonable measure of oxygen saturation of the blood in the region.

Protoporphyrin IX (PpIX), formed in tissue from 5-ALA as part of the heme synthesis pathway that is upregulated in many tumors, absorbs across the visible spectrum, with a large absorption in the blue Soret band. This absorption leads to fluorescence emission from PpIX in the 640-720 nm wavelength range. In an embodiment, incident radiation stimulates emission of blue Cherenkov radiation within the subject, which in turn stimulates fluorescent light emission by PpIX; some of the fluorescent light from the PpIX is then emitted from the subject and imaged.

Light emitted from the subject 102, both of Cherenkov origin as modulated by absorption in tissue and tumor, and of fluorescent (or phosphorescent) origin, and attenuated by molecular absorbers in the subject, is captured 212 by fibers 114 or camera 117. This light is directed to multichannel spectrographic detector 116, which performs a spectral analysis of received light. Electronic spectrographic signals indicative of light amplitude at each of several wavelengths of interest are provided from spectrographic detector 116 to processor 118 for processing.

In an embodiment, processor 118 utilizes a model of light propagation from the beam path through a model of subject 102 to determine a spatial model of light emitted within, and light attenuation within, subject 102 and tumor 104. It is expected that such an embodiment could offer enhanced accuracy over an uncorrected system. In an embodiment, a Monte-Carlo photon propagation model is used.

In an alternative embodiment, beam 110 is directed at tumor 104 from multiple angles through tissue 112 within each treatment session. In such an embodiment, processor 118 uses information regarding beam angle to correlate measurements such that tumor oxygenation and tumor metabolic activity determined during one session is compared with tumor oxygenation and metabolic activity determined along a similar beam angle in other sessions.

Processor 118 quantifies Cherenkov emission 216 in tumor and total hemoglobin from an amount of light measured at one or more wavelengths to which oxyhemoglobin and deoxyhemoglobin are isosbestic.

Processor 118 quantifies percent oxygenation 218 of hemoglobin in tumor from light quantity received at 2 specific wavelength bands such as bands centered at 750 nm and 580 nm wavelengths. Alternatively the measured spectral characteristics of light captured by fibers 114 are curve-fit to pre-measured Cherenkov emissions spectra and transmission attenuation data obtained from samples of liquid with blood and water that have been oxygenated and deoxygenated.

Processor 118 quantifies metabolic activity 220 of tumor by quantifying fluorescent emission from PpIX by quantifying received light from fibers 114 in the 640-720 nanometer wavelength band, and applying any corrections provided in the embodiment. In alternative embodiments, these corrections may include corrections from a Monte-Carlo or diffusing photon propagation model of the tissue.

The stimulation of fluorescence emission by protoporphyrin IX can be taken as a signal which is proportional to the amount of PpIX produced, and this is indicative of metabolic activity in the tumor. Destruction of cellular mitochondrial function through radiation damage due to the applied radiotherapy would appear in some embodiments as a reduction of PpIX production, and hence a decrease in light emitted at PpIX fluorescent wavelengths versus light emitted at Cherenkov wavelengths in the detected spectrographic signals.

In an alternative embodiment, fluorescent emissions from another metabolite are used as a fluorophore for tracking metabolic activity of tumor 104, the fluorophore being excited by the Cherenkov radiation. In alternative embodiments, the fluorescent emission could be used to track the activity of an alternative enhancement agent, such as antibodies or antibody fragments to cell surface receptors tagged with a fluorescent (or phosphorescent) dye. In yet other alternative embodiments, fluorescent emissions from NADH or NAD excited by the Cherenkov radiation are used as indicators of metabolic activity within tumor 104.

Since radiation damage to tumor cells during radiotherapy involves free radical reactions, it is expected that treatment effectiveness will depend somewhat on the relative oxygenation of heme at the tumor 104 as monitored by processor 118. Further, changes in metabolic activity in tumor 104 from a first treatment session to a later second treatment session as measured by PpIX or other fluorescent emissions measured by processor 118 are also expected to be indicative of treatment effectiveness. In fractionated radiotherapy subjects may receive as many as 30 to 40 fractions of a total radiation dose, each fraction being administered on a separate day as part of a total treatment series. During the treatment series, changes in tumor metabolic activity are expected if the tumor is responsive to therapy. It is expected that metabolic signal changes would occur as a decrease in the fluorescent signal over time if the patient is responding to therapy.

These measures of treatment effectiveness are presented to a physician and used to adjust 222 the treatment plan, both of the radiotherapy and following adjunct therapies such as chemotherapy.

In an embodiment, multiple spectrographic analyzers are provided, each coupled to receive Cherenkov and fluorescent emissions from a different point on the subject through separate pickup fibers. In this embodiment, diffuse optical modeling or Monte Carlo modeling software executing on processor 118 allowing reconstruction of a shape and spectral characteristics of an emissions zone within the subject, and for determining spectral characteristics of light emitted within the tumor as opposed to light emitted elsewhere (such as in normal tissues) in the subject by compensating for changes due to light transport in surrounding tissues. The diffuse optical modeling software provides for more accurate estimation of the fluorescent emissions thereby refining the measurements to more directly inform about pertinent areas of tissue.

In an alternative embodiment, light emissions from the subject are sampled only from certain predetermined beam locations or from certain predetermined locations within the subject, with the goal of maximizing information from non-tumor tissues. Also, in an alternative embodiment, comparison of measurements of emitted light spectra from tumor and non-tumor regions is performed to accurately calibrate data to the individual subject, making interpretation of changes over different days more reliable.

In an alternative embodiment, in addition to collecting fibers 114 placed at a surface of subject 102, there are additional optical collecting fibers (not shown) placed within body cavities or, in some alternative embodiments, even directly implanted in tumor 104. Light from such fibers is processed by spectrographic detector 116 and processor 118 in a manner similar to that stated herein for light from fibers 114. Such additional collecting fibers may permit improved accuracy by enabling the system to track light signals which do not propagate well in tissue, or minimizing the spectral distortion of light passing through tissue to the detector. In an alternative embodiment, implantation of fibers onto surfaces or in cavities is incorporated as part of radiation therapy preparation.

Measurement of emission stimulated by radiation emitted from implanted radio-isotope sources, such as brachytherapy seeds is feasible, and can allow direct measurement at the tissue site where the radiation is imparting maximal energy. Implanting fiber optic measurements at these sites is feasible via fiber optics or small photodiode arrays. Following the same procedures as above, the tissue function or blood oxygen saturation could be probed during the prolonged delivery of radiation during brachytherapy radiation delivery.

Many sources of high energy charged-particle beams, including cyclotrons and some other particle accelerators, including some linear accelerators, provide pulsed beams. Further, the human visual system is known to integrate received light, so that black intervals that are short enough, and repeated rapidly enough, may not be noticed by a human subject. In an alternative embodiment, therefore, the enclosure 106 is omitted. The treatment room is sealed to exclude all natural and uncontrolled artificial light. Timing interfaces 120 are provided for determining intervals of beam transmission, and for controlling pulsed room lighting 122.

Figure 5:
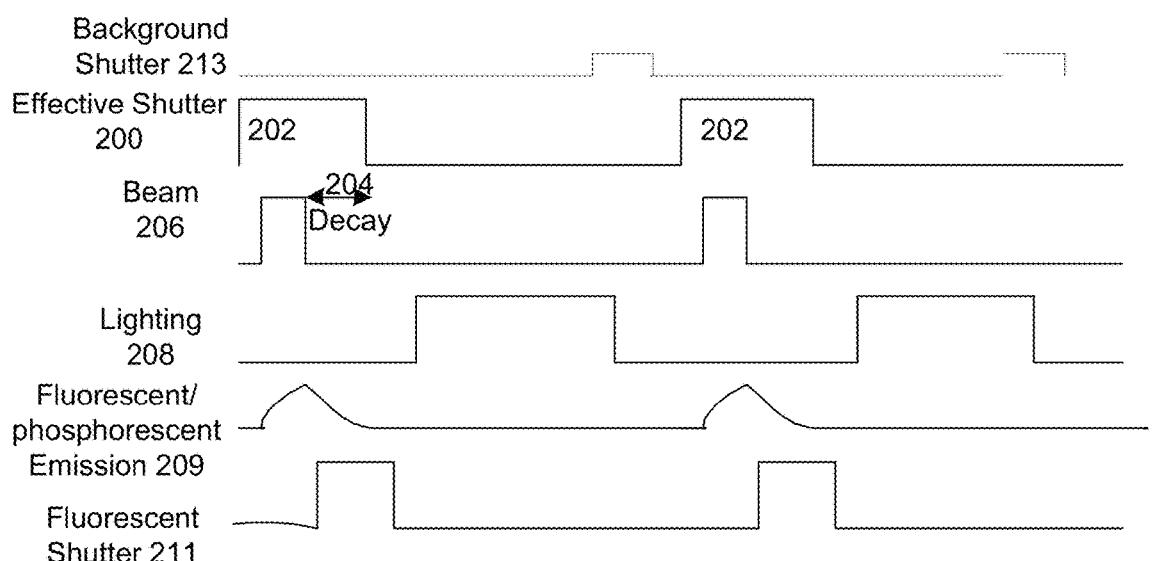
FIG. 5 is an approximate timing diagram of time windows showing relationships of room lighting, beam pulses, and camera shutter windows.

In operation, the timing interfaces 120 controls an effective shutter (FIG. 5) interval 200 of the spectrographic detector 116 to effectively consider only light received by the cameras in an interval 202 during and/or surrounding pulses of, and including a fluorescent decay interval 204 after, pulses 206 of the beam. Timing interfaces 120 also controls and pulses room lighting such that the shutter interval does not overlap pulses 208 of the room lighting. Light received at the spectrographic detector 116 during multiple shutter intervals is totalized, in an embodiment at the camera, and in an alternative embodiment multiple images are captured and per-channel spectrographic light totals are totalized by processor 118.

Figure 3:
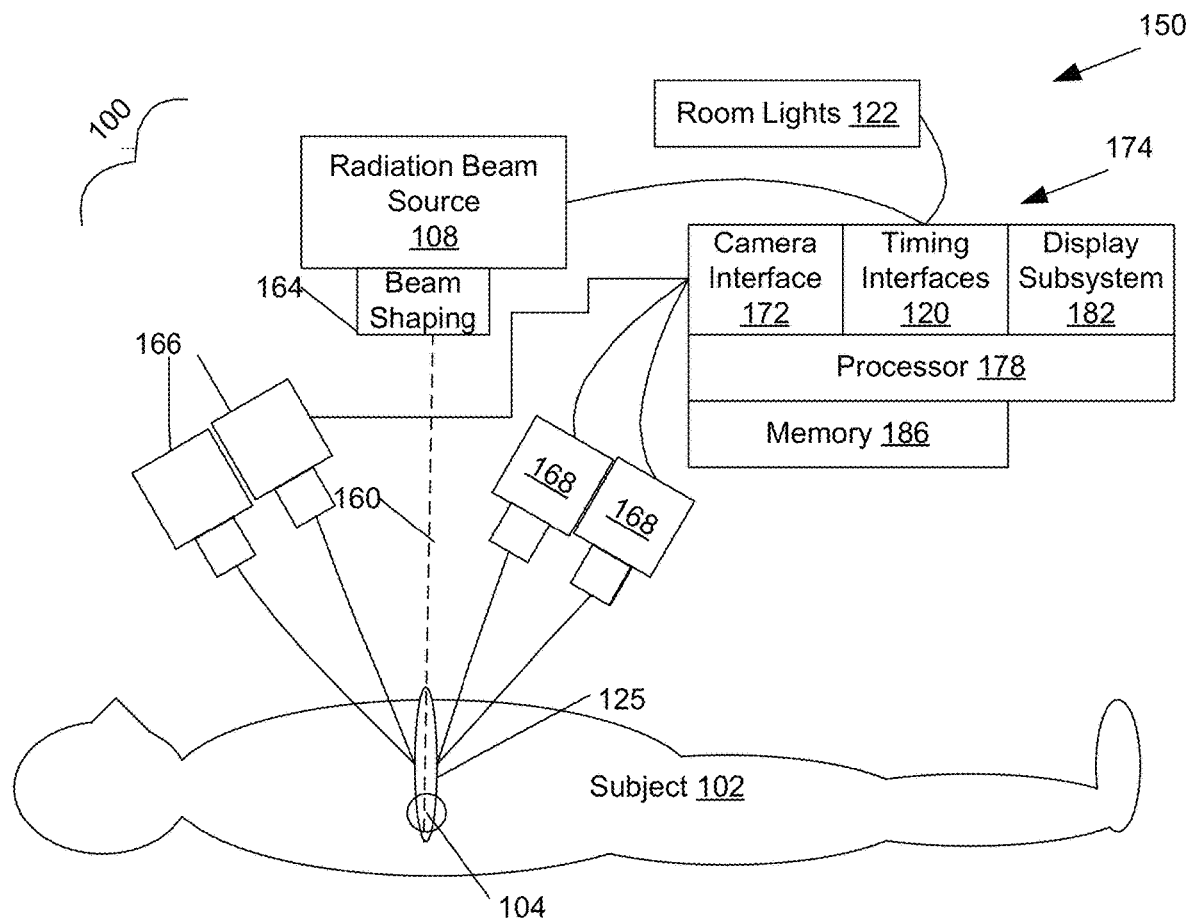
FIG. 3 is an illustration of an alternative embodiment of a system for performing monitored radiotherapy with time-controlled room lighting and camera sensing of light emissions from a subject.

In an alternative embodiment 150 (FIG. 3), as an alternative to optical fibers 114 and multichannel spectrographic detector 116, high-sensitivity electronic cameras 166, 168, are used to image Cherenkov light and localize locations on the subject where this light is emitted. In another alternative embodiment, some optical fibers 114 and multichannel spectrographic detectors 116 are provided, with the fibers placed in particular tumor locations, and electronic cameras 166 are provided for imaging light escaping from the subject.

A subject 102 is placed in the path of a radiation beam 160 such that the beam intersects tumor 104. Beam 160 is provided by an accelerator 108, or other device for providing high energy radiation, and is typically shaped by beam-shaping apparatus 164.

The subject 102 is located within an environment that excludes daylight, and light from uncontrolled sources, such as incandescent lamps, is also excluded.

In an embodiment, a drape or paint of a light-absorbing material is provided so that stray light emitted from the subject 102 and not absorbed by a camera 166, 168 is absorbed.

In an embodiment, the accelerator 108 provides a beam of electrons having energy of 6 million electron volts (6 MeV)

or greater, as used to provide treatment energy to deep tumors as opposed to treatment of surface skin. In a particular embodiment the beam energy lies between 6 and 24 MeV. In an alternative embodiment, the accelerator 108 produces a photon beam of 6 MeV or greater. In another alternative embodiment, the accelerator 108 provides a high-energy proton beam. In an alternative embodiment, an electron beam having electron energy of 0.5 MeV or greater is used.

At least one camera 166 is used to capture the images, and in an embodiment a second or more cameras 168, are positioned to provide multiple images of Cherenkov and fluorescent radiation emission from subject 102. In an embodiment, multiple cameras with a defined linear and angular spacing between them at each camera location are provided.

The cameras 166, 168 are coupled to camera interface 172 of image processing system 174; camera interface 172 captures and stores digital images from the cameras 166, 168, in memory 176 for processing by at least one processor 178 of the image processing system 174. In addition to interfaces to the camera interface 172 and memory 176, processor 178 interfaces with a timing interface 120 and a display subsystem 182. Timing interface 120 is adapted to determine timing of pulses of radiation from the radiation beam source 108, to control pulsed room lighting 122 to avoid interference from room lighting in the way discussed with reference to FIG. 5, and to synchronize light or image capture by spectrographic detector 116 or cameras 166, 168 at shutter intervals discussed with reference to FIG. 5.

In an alternative embodiment, instead of blanking room lighting during pulses of the radiation beam, room lighting is left on, but subdued. The image processor is configured by machine readable instructions to operate the camera twice for each Cherenkov-light image. The camera is operated to obtain a first image during the time the radiation beam is ON; this image is exposed by both room lighting and by Cherenkov light. A second image is then obtained during a nearby time, and for an equivalent shutter period, when the radiation beam is OFF, and therefore is exposed by room lighting alone. The Cherenkov-light image used for further processing is determined by the image processor by subtracting the second image from the first image, leaving an image corresponding to an image taken under Cherenkov light alone.

In yet another alternative embodiment, during a radiation treatment the room lighting is replaced by a subdued, monochromatic, light at a first wavelength or first wavelength band. This may, for example, be light provided by light-emitting diodes. The Cherenkov-light images are obtained at wavelengths other than the first wavelength by use of a notch filter that blocks light of the first wavelength or wavelength band. Since Cherenkov emissions are typically broadband, albeit more intense toward the blue end of the spectrum, a Cherenkov-light image that excludes light of the first wavelength, but includes other wavelengths, is adequate for determining beam shape and intensity of skin irradiation. For example, the first wavelength may be a green wavelength. Cherenkov light emitted at the skin surface can be visualized by imaging at blue wavelengths, and, since heme in tissue blocks many short wavelengths of light, Cherenkov light emitted at deeper levels in tissue may be visualized by imaging at wavelengths in red wavelengths. Cherenkov-stimulated fluorescent and phosphorescent emissions may also be visualized by imaging at wavelengths in the infrared and red visible wavelengths.

As the beam penetrates subject 102, Cherenkov light is emitted within an emissions zone 125, including the tumor 104.

In an embodiment, the imaging system cameras 166, 168 are spectrally-sensitive cameras capable of providing spectral data permitting distinction between Cherenkov and fluorescent light, and in a particular embodiment permitting distinction between oxyhemoglobin and deoxyhemoglobin. Spectrally-sensitive cameras suitable for this application may be implemented as black and white cameras equipped with apparatus for positioning and changing filters in front of each camera, such as rotatable multiple-filter disks; by deposition of custom filter elements in a pattern on pixel sensors of a photosensor array as is common for color cameras; or in other ways.

In embodiments, raw or de-noised images from the imaging system are recorded in a suitable digital memory system as documentation of the radiation treatment.

While Cherenkov radiation is emitted during beam pulses 206 (FIG. 5), light emitted 209 from naturally occurring, artificially administered, and drug metabolite fluorescent materials within a subject, including PpIX, lags the beam and decays exponentially after each pulse of the beam turns off as illustrated. In an embodiment therefore, an effective shutter interval during beam pulse 206 is used to image light primarily emitted by Cherenkov mechanisms, and an effective fluorescent-emissions shutter interval 211 is used to capture light emitted from the subject or phantom by fluorescent and phosphorescent mechanisms. In this embodiment, light arriving in fibers 114 or light imaged by cameras 166, 168, is recorded as image pairs, with a first image of each pair indicative of light emitted during beam pulse 206 and a second image of each pair indicative of light emitted during the fluorescent shutter interval 211. Processor 118 or 178 executes machine-readable instructions in associated memory, such as memory 186 to reconstruct first tomographic image sets of the subject from the first images of all image pairs captured, to reconstruct second tomographic image sets of the subject from the second images of all image pairs captured, and the ratios or otherwise processes the first and second tomographic image sets to determine a tomographic image set of fluorophore distribution in the subject.

In embodiments, such as those where 5-ALA is administered, where fluorophore distribution is related to metabolic activity in the subject, the tomographic image set of fluorophore distribution in the subject is also indicative of metabolic activity in the subject. The processor 118 or 178 further executes machine readable instructions in memory to compare the tomographic image set of fluorophore distribution in the subject against a tomographic image set of fluorophore distribution obtained during a prior radiation treatment session to produce a tomographic image set indicative of treatment effectiveness.

Since both an enclosure 106 surrounding and excluding ambient light from the subject, and the combination of timing interfaces 120 and pulsed room lighting 122 serve to prevent interference of room lighting from interfering with measurement of Cherenkov radiation and fluorescent radiation emitted from an emissions zone in the subject, the term "apparatus for preventing interference by room lighting" as used herein shall mean either or both of an enclosure 106 surrounding and excluding ambient light from the subject, and the combination of timing interfaces 120 and pulsed room lighting 122.

Cherenkov radiation and associated fluorescent emissions are useful for beam profiling and calibration as well as for monitoring treatment.

Figure 4:
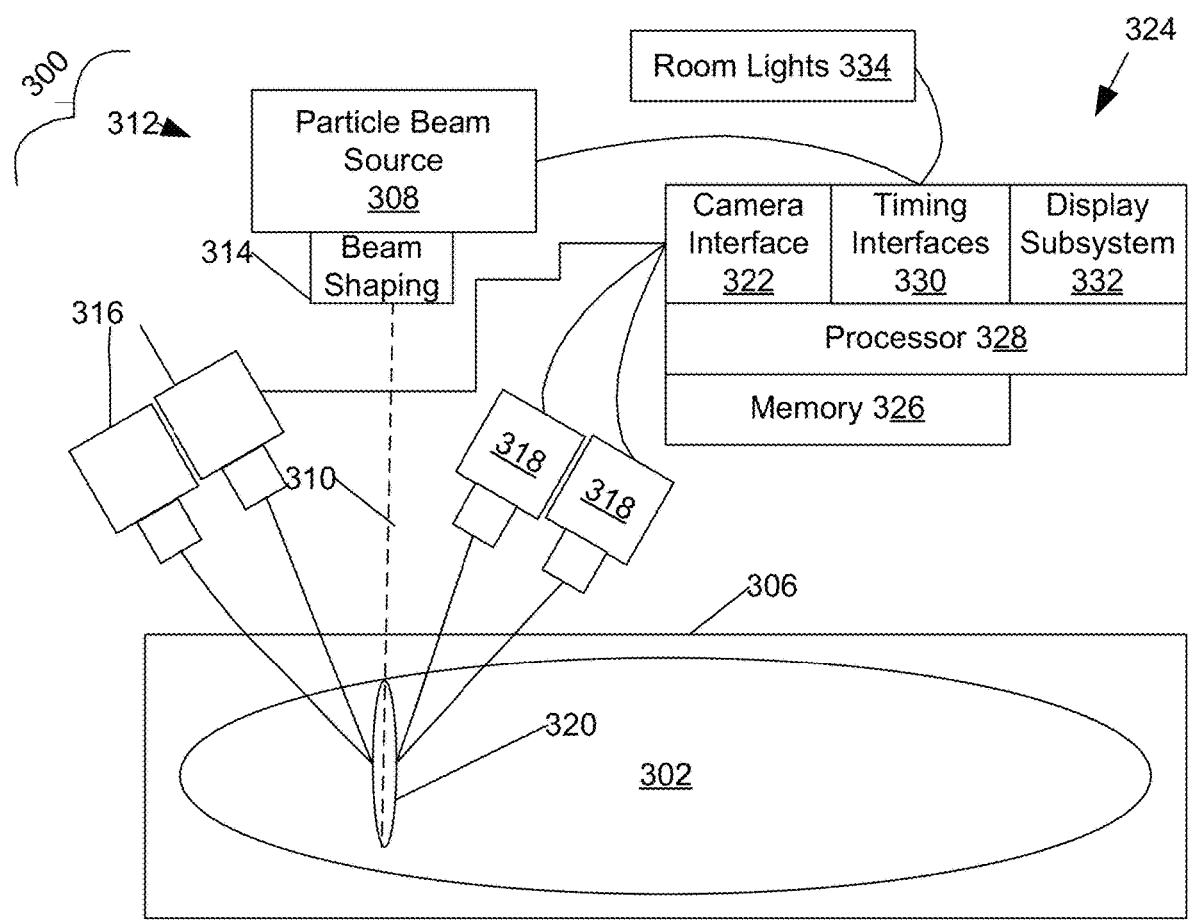
FIG. 4 is a block diagram of apparatus for determining beam profiles of high energy radiation for use in radiotherapy.

A system 300 for providing radiotherapy equipped with a subsystem for determining beam profiles is illustrated in FIG. 4.

A beam-calibration phantom 302 is placed in a zone where it is desired to measure a profile of a radiation beam 310 provided by a radiation treatment machine 312. The zone may be a volume above or beside a treatment table 306. In many embodiments, the phantom is a fluid-filled tank, the fluid in the tank being a transparent fluid having an index of refraction greater than that of air; in a particular embodiment the transparent fluid is water. In an embodiment, the tank has transparent top and sides such as glass or transparent plastic. In a particular embodiment the tank has sides constructed of acrylic sheets; another particular embodiment has sides constructed of polycarbonate panels. In an embodiment, a small amount of scattering agent is added to the liquid in the tank to enhance scatter of Cherenkov light but not affect propagation of the radiation beam, overcoming directionality of Cherenkov light and allowing more light to be detected laterally around the tank. The treatment room may be blacked out to prevent interference of ambient light with measurements of the Cherenkov radiation because a phantom is not subject to claustrophobia like live subjects.

In an alternative embodiment, the tank is filled with a transparent fluid having an index of refraction greater than that of water, such as silicone oil. In yet another embodiment, the phantom is formed from a high-index, transparent, material, such as a cast high-index plastic, and may have both fluorophores and light-scattering additives embedded within it.

The treatment table 306 and phantom 302 are located within an environment that excludes daylight, and light from uncontrolled sources, such as incandescent and fluorescent lamps, and LED indicator lights, is also excluded. In another embodiment, the phantom walls are coated on their interior surface with a light-absorbing coating except for camera viewing windows positioned in front of each camera, the coating is provided to absorb both stray light originating from outside the phantom and to prevent Cherenkov light from being reflected from the phantom wall into a camera to give a false indication of beam profile.

In an embodiment, a drape of a light-absorbing material is provided so that stray light emitted from Cherenkov radiation zone 320 and not absorbed by a camera is absorbed without being scattered back to the treatment zone. The light-absorbing drape improves contrast in Cherenkov images by reducing stray light.

An accelerator 308, or other device for providing high energy radiation, is aimed to provide a beam 310 of radiation through beam-shaping apparatus 314 to phantom 302. In an embodiment, the accelerator 308 provides a beam of electrons having energy of 6 million electron volts (6 MeV) or greater, in a particular embodiment the beam energy lies between 6 and 24 MeV. In an alternatively embodiment, the accelerator 308 produces a photon beam of 6 MeV or greater. In an alternative embodiment, the accelerator 308 provides a proton beam. In an alternative embodiment, the accelerator 308 produces a beam of electrons or photons having a substantial percentage of electrons or photons having energy of 1 MeV or greater.

Figure 6:
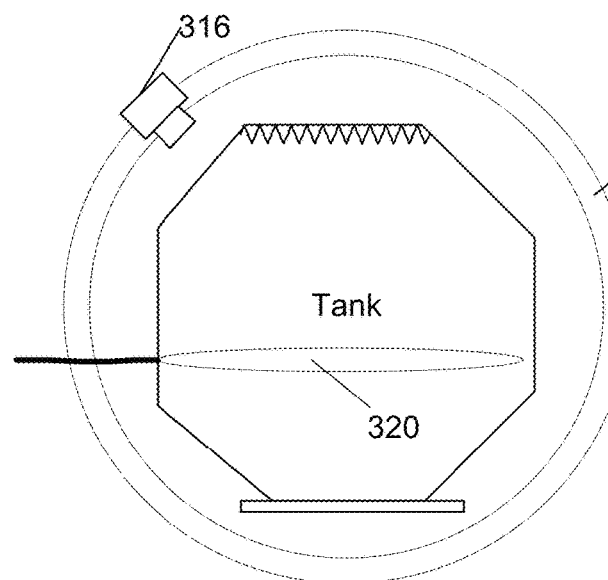
FIG. 6 illustrates a system utilizing a single camera, or camera pair, on a rotating mount for determining profiles of high energy radiation for use in radiotherapy.
Figure 7:
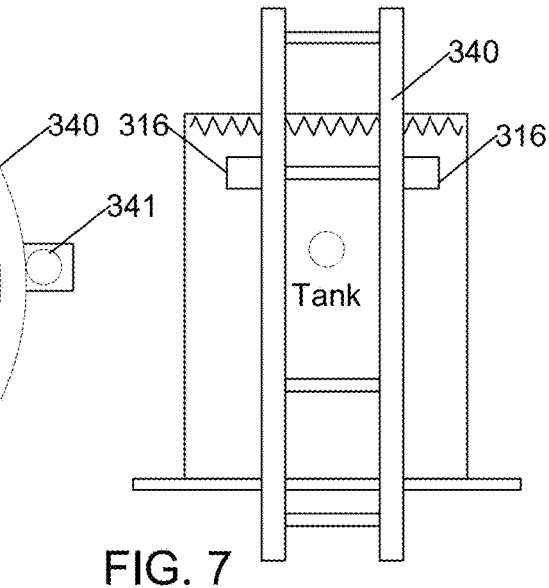
FIG. 7 illustrates the system of FIG. 3 from a different angle.

At least one camera 316 is used to capture the images, and in an embodiment a second or more cameras 318, are positioned to provide multiple images of the Cherenkov radiation emission zone 320 where beam 310 intersects the transparent fluid of phantom 302. In an embodiment, as illustrated in FIG. 4, a pair of cameras is used by providing two cameras 316 with a defined spacing between them at each camera location, allowing imaging of the beam with or without tomographic recovery. In an alternative embodiment as illustrated in FIG. 6, a single camera 316; or in a variation as illustrated in FIG. 7, a single camera pair 316 is provided; the embodiments of FIGS. 6 and 7 mount the camera or camera pair on a rotary, movable, mount 340 such that single images, or stereo pairs of images, can be made of the Cherenkov emissions zone from several camera positions, In the interest of simplicity, structure and bearings for supporting the rotary mount 340 and motor 341 has not been shown. The embodiment of FIG. 7 illustrates the beam entering the tank from out of the page.

Figure 8:
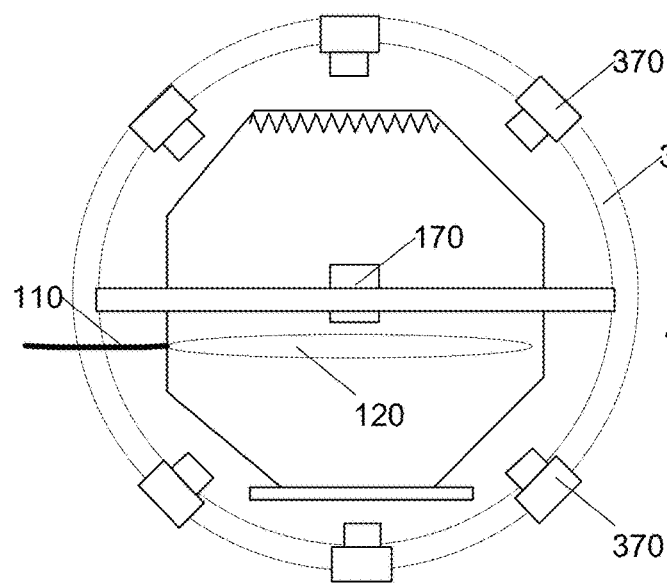
FIG. 8 illustrates a system having multiple cameras on a fixed mount outside the tank.
Figure 9:
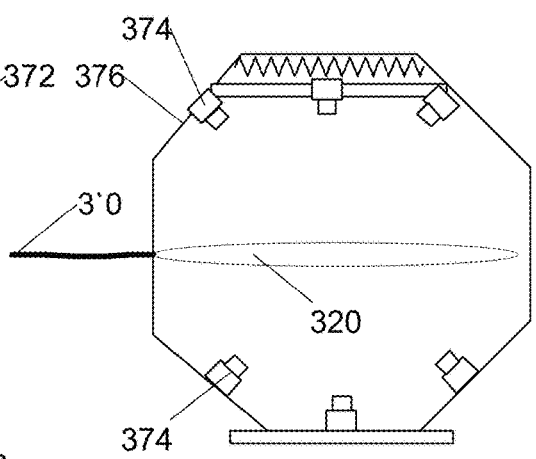
FIG. 9 illustrates a system having multiple cameras mounted inside the tank.
Figure 10:
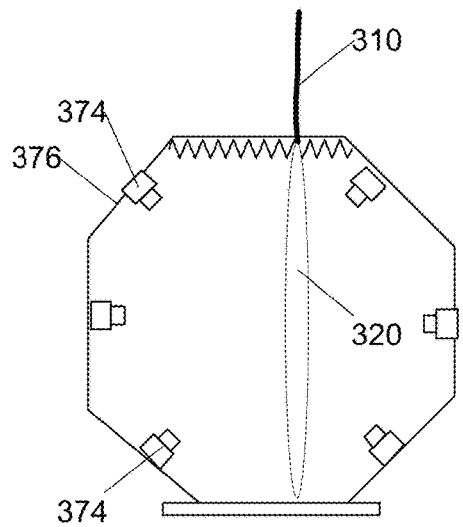
FIG. 10 illustrates a system having the beam enter the tank from above the tank.

While the embodiments of FIGS. 6, 7, 8, and 9 illustrate the beam entering the tank from a side of the tank, the method is applicable to beams entering the tank from any angle, including by way of example a beam as illustrated in FIG. 10. where the beam comes from above the tank.

The cameras 316, 318 are coupled to camera interface 322 of image processing system 324; camera interface 322 captures and stores digital images from the cameras 316, 318, in memory 326 for processing by at least one processor 328 of the image processing system 324. In addition to interfaces to the camera interface 322 and memory 326, processor 328 interfaces with a timing interfaces 330 and a display subsystem 332.

In an alternative embodiment, as illustrated in FIG. 8, a plurality of cameras 370 are disposed on a fixed frame 372 outside the volume of the phantom but configured to provide images of the emissions zone 320 from several angles.

In an alternative embodiment, as illustrated in FIG. 9, a plurality of submersible cameras 374 are disposed within the volume of the phantom and configured to provide images of the emissions zone 320 from several angles. In a particular embodiment, submersible cameras 374 are cemented to a wall of phantom 376.

In a particular embodiment, a camera is disposed to image the emissions zone from approximately every 60 degrees in the horizontal plane, into which the radiation beam is being sent. The camera field of view is designed to capture the relevant depth of the beam into the tank from above, and the depth of focus of the cameras is designed to capture light from the entire cross section of the beam. The angular arrangement is chosen to allow capture of the beam profile data in a time which matches with the temporal requirements of characterizing the beam. For example, fast beam profile changes or complex beam cross section shapes require more cameras and less mobile cameras, for fast profile imaging.

Camera numbers and viewing angles may in some embodiments be determined according to the expected beam profile; for example standard square beam cross sections may only require one or two cameras to characterize the beam, and may not even require tomographic recovery to characterize the beam. Where imaging time is unconstrained, beams may be imaged with a rotation stage or rotating frame for sequential imaging of the beam from multiple angles. A standard square beam may be adequately profiled by only two camera positions at 90 degrees from each other, whereas a non-square or non-circular beam would require more camera positions for tomographic recovery of the profile. If adaptive delivery of radiation such as arc therapy or intensity modulated radiation therapy are imaged, then multiple parallel cameras would be desirable to allow imaging of the complex beam cross sections in reasonable or in real time during delivery to the tank. The time constraints and complexity of the beam therefore determine the exact number of cameras and degree of sequential or parallel acquisition.

Figure 11:
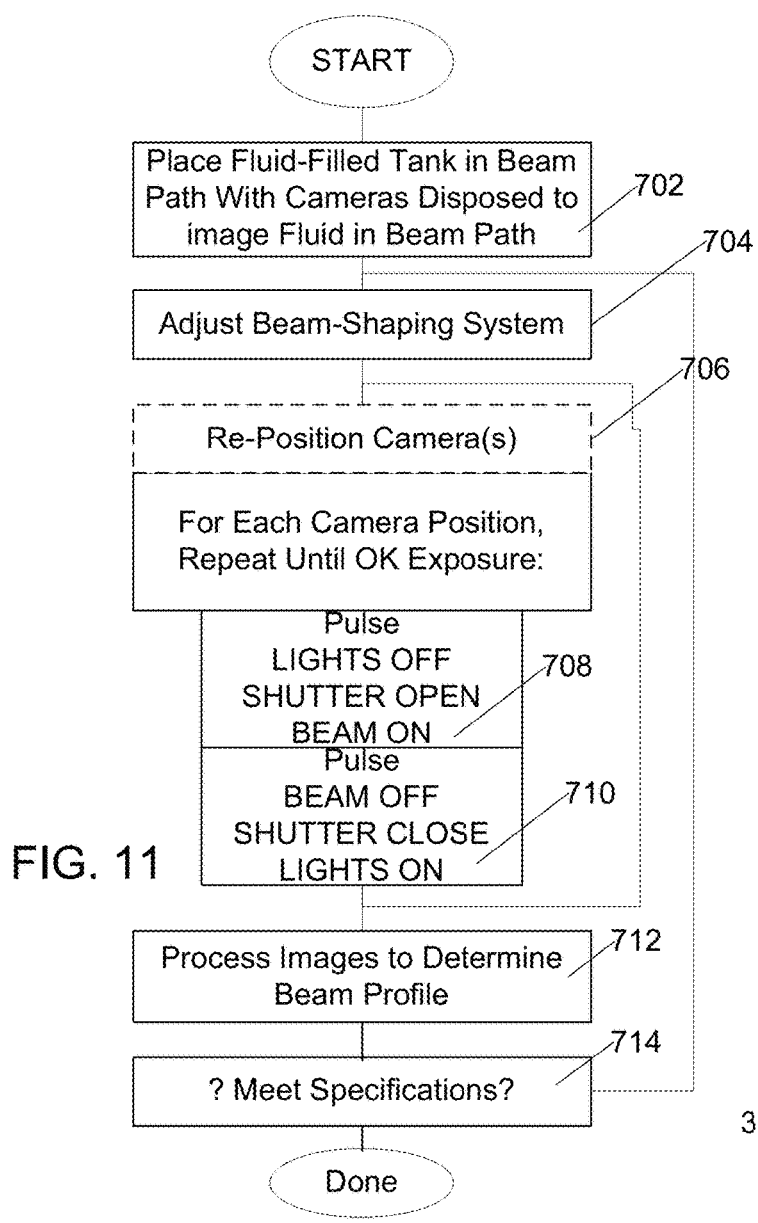
FIG. 11 is a flowchart of a method of determining beam profiles of high energy radiation for use in radiotherapy.
Figure 12:
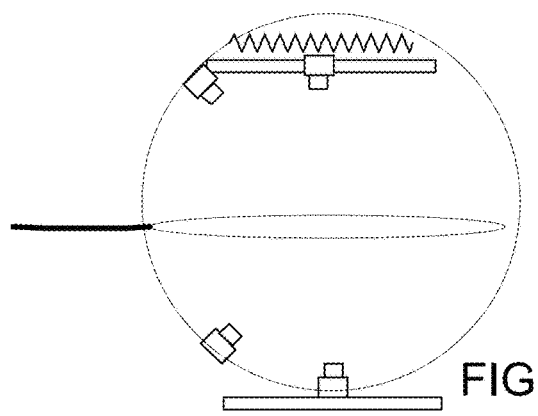
FIG. 12 is an illustration having a spherical or cylindrical tank with internal cameras, with the tank mounted on a rotary mount.

In each embodiment, as illustrated in FIG. 11, the tank is positioned 702 in the beam, and beam adjustment devices, if any, are adjusted 704 to provide a particular beam profile. The cameras 316, 318, 370, 374 in all embodiments are disposed to provide images of the Cherenkov radiation emissions zone 320, where beam 310 intersects fluid of phantom 302, and may be repositioned 706 if movable camera mounts are used. It should be noted that, because cameras are likely to be damaged if the beam directly impinges on the camera, movable mount 340 is configured, and the cameras are located, to avoid direct impingement of the beam on any camera.

In each embodiment, images and/or stereo pairs of images each are taken by sequentially 708 turning OFF room lighting, opening effective or physical camera shutters, pulsing the beam, then sequentially 710 turning off the beam, closing shutters, and turning ON room lighting. This process results in multiple images taken from multiple angles of Cherenkov radiation zone 320 by cameras 316, 318, 370, 374. Once sufficient images are captured, they are processed 712 by processor 328 to generate a fully three dimensional image of the Cherenkov emission. These images are then used to tomographically reconstruct the beam profile.

Prior to reconstruction of the beam profile from the images, the images obtained by any cameras located outside the phantom volume (such as those of FIGS. 4, 6, and 8) are corrected for distortions caused by refraction as light passes from the emissions zone 320 through known surfaces of the phantom.

A combination of rotation angles both vertical and lateral around the beam may be used.

The multiple camera image formation by tomography would use a filtered backprojection computational algorithm for recovery of the emissions zone 320.

It is known that Cherenkov emissions from beams of intensities used during radiotherapy are somewhat dim, hence sensitive cameras with long, integrated, exposures are required, and it is also advisable to avoid interference from extraneous lighting sources. In an alternative embodiment, sensitive cameras take multiple short exposures, the multiple exposures being summed to provide an overall integrated exposure.

Timing interfaces 330 are arranged to sense a timing of beam pulses provided by particle beam source 308 and to control room lighting 334 such that room lighting is pulsed and does not overlap pulses of beam 310. Similarly, timing interface 330 is arranged to control capture of images at camera interface 322 from stereo camera pairs 316, 318 to capture images of light emitted at emission zone 320 during pulses of beam 310, and to ignore light received by camera pairs 316, 318, during pulses of room lighting. It is anticipated that room lighting 334 may be provided by fast-responding light-emitting diode arrays.

In operation, the timing interfaces 330 controls an effective shutter (FIG. 5) interval of the cameras or stereo camera pairs 316, 318, 370, 374 to effectively consider only light received in an interval 202 surrounding pulses of the beam. The timing interfaces 330 also controls and pulses room lighting such that the shutter interval does not overlap pulses of the room lighting. Light received at the cameras 316, 318, 370, 374 during multiple camera intervals is totalized, in an embodiment at the camera, and in an alternative embodiment multiple images are captured and pixel light totals are totalized by processor 328.

Once sufficient light is received at cameras 316, 318, 370, 374 during the shutter intervals and totalized images prepared in or read through camera interface 322 into memory 326, the beam is shut off. Then at least one processor 328 then processes the images in memory 326, to construct a three-dimensional model of light emissions in the emission zone 320. Since the light emissions in the emissions zone are from Cherenkov radiation emitted as charged particles of beam 310 decelerate in the fluid of the phantom, with broadband spectral constituents decreasing with wavelength to the inverse square power, these light emissions relate directly to radiation dose from beam 310 passing into and absorbed in the emissions zone 320. Further, since Cherenkov radiation is emitted from where the beam intersects fluid of the phantom in emissions zone 320, and not from surrounding un-irradiated fluid, the reconstructed three dimensional model of light emissions in emissions zone 320 provides an indication of beam shape.

The processor 328 then uses display subsystem 332 to provide displayable images illustrating cross section, overall surface, and tomographic images representing radiation dose profile in the emissions zone 320. In a particular embodiment, processor 328 has at least one processor as known in the art of computing coupled to execute instructions from a memory system; in an embodiment the memory contains machine readable instructions for processing multiple sets of images to construct the three-dimensional models of light emissions in the emission zone 320, and to prepare displayable images representing radiation dose profile in the emissions zone; the memory containing machine readable instructions may be the same or a different memory than the memory 326 in which images are stored.

In an embodiment, processor 328 has calibration information in its memory system, and translates the determined three dimensional models of Cherenkov light emission in the emissions zone into three dimensional models of radiation intensity and/or dose.

Monte Carlo simulations are used to study the complex directionality of Cherenkov radiation at each spatial location within the irradiated tank. Due to the finite field of view of the cameras, the intrinsic proportionality between the imparted dose and emitted Cherenkov radiation may be distorted. Therefore necessary calibration factors may be sought through analysis of the system and its camera placements. Additional correction factors may be necessary to correct for inherent differences between the emitted Cherenkov light and imparted dose, specifically spatial locations where the relative fluence of low keV energy electrons is high.

Because fluorescent emissions are omnidirectional, a fluorophore or fluorescent dye in a phantom helps overcome distortions that may otherwise result due to the directionality of emitted Cherenkov radiation, whether the charged particles are part of a charged-particle radiation beam or induced by high-energy photons of a gamma-ray photon beam.

Since high index materials may absorb radiation differently than does tissue, in an embodiment processor 328 has calibration information in its memory system for adjustment for beam attenuation in the phantom, and translates determined three dimensional models of light emission in the emissions zone into three dimensional models of radiation dose in tissue using that calibration information.

While Cherenkov radiation is emitted during beam pulses 206 (FIG. 5), light emitted 209 from fluorophores lags the beam and decays exponentially after each pulse of the beam turns off as illustrated. In an embodiment therefore, an effective shutter interval during beam pulse 206 is used to image light primarily emitted by Cherenkov mechanisms, and an effective fluorescent shutter interval 211 is used to capture light emitted from the phantom by fluorescent and phosphorescent mechanisms. In this embodiment, light imaged by cameras 316, 318 is recorded as image pairs, with a first image of each pair indicative of light emitted during beam pulse 206 and a second image of each pair indicative of light emitted during the fluorescent shutter interval 211. Processor 328 therefore executes machine-readable instructions in associated memory, such as memory 326 to reconstruct beam shape and beam energy distribution profiles from the captured image pairs.

In an alternative embodiment, in order to increase sensitivity and improve contrast, images obtained during and after 211 multiple pulses 206 of the beam are summed and/or averaged.

In an embodiment, an operator may turn on the beam, and have the system construct a model of emissions zone 320, then turn off the beam and view the images provided on display subsystem 332. If the beam fails to meet specifications 714 for a particular treatment, the operator may then use the images provided on display subsystem 332 to determine a different setting of beam-shaping apparatus 314 that should provide a beam that more closely resembles a beam desired for treatment of a patient. The operator may then adjust beam shaping apparatus 314, following which the beam is turned back on while new images of Cherenkov radiation in emissions zone 320 are captured by the cameras 316, 318, 370, 374, the beam then being turned off and a new three-dimensional model of the emissions zone and displayable images prepared. Once beam profile meets a desired beam profile, the phantom is removed and replaced by a patient, and the system may then be used to provide radiation of the desired profile for treating the patient.

In an embodiment, parameters of the three dimensional model of the emissions zone and the displayable images are recorded in a machine-readable memory system, such that the model and images may be used to document treatment, for periodic quality assurance and calibration, or to seek regulatory approvals. In another embodiment, the parameters of the three dimensional model are used to satisfy monthly quality assurances checks on the clinical electron and x-ray photon beam qualities.

In an embodiment, the system is utilized with optically translucent anthropomorphic tissue phantoms, or complex tissue phantoms to capture images of the beam shape in more complex geometries and tissue compositions than is possible in homogeneous water phantoms.

Motion Systems for Skin Dose and Beam-Skin Intersection Tracking

As is known in the art of radiotherapy, the relative positions of subject and beam source is often altered during treatment. For example, a subject may be rotated in a radiation beam, or more commonly the radiation source is rotated about the subject, to irradiate a tumor within the patient from multiple angles, and thereby spread out radiation dose received by normal tissues of the subject. In an embodiment, surface images of Cherenkov emission from tissue are repetitively captured during standard courses of fractionated radiotherapy, and these images provide real time video of beam delivery on the subject's tissue, both for relatively stationary and relatively moving beam and subject. Further, the images can be used as real time video or integrated to provide an estimate for total skin dose. The images can be acquired from gated cameras set up inside or alongside the linear accelerator to image skin illuminated by the accelerator or at fixed positions within the treatment room. In embodiments utilizing fiducial markers placed on or in tissue, the images have both information about the delivered dose map on the tissue as well as biological fiducial information, and both can be used in treatment verification.

Figure 13:
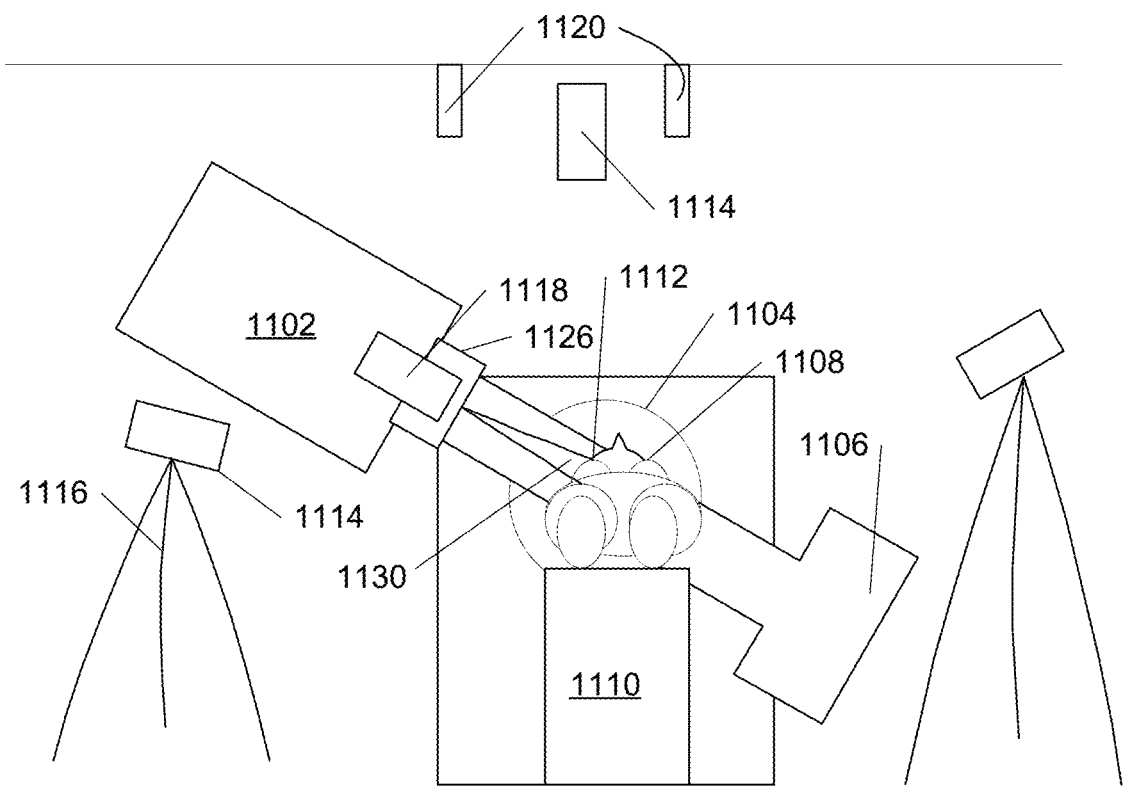
FIG. 13 is an illustration of a radiation treatment system having realtime observation of skin dose using Cherenkov radiation emitted by the interaction of beam and skin.

In an embodiment, as illustrated in FIG. 13, a movable particle accelerator 1102 on rotary mount 1104 and counterweight 1106 with a subject 1108 positioned on a table 1110, such that the accelerator 1102 may rotate about subject 1108 to provide radiation treatment to a breast 1112 of subject 1108. One or more intensified CCD (ICCD) cameras 1114 are positioned on tripods 1116, suspended from ceiling of a room enclosing the accelerator, or attached 1118 to the accelerator 1102. At least two optical cameras, such as a stereo pair of cameras 1120, are also provided. Accelerator 1102 may be equipped with a multi-leaf collimator 1126. All cameras, including ICCD cameras 1114 and stereo optical cameras 1120 are interfaced (connections are not shown for simplicity) through a camera interface 1122 to an image processor 1124 that has memory 1128 having recorded therein machine readable code for performing the steps referenced below with reference to FIG. 15. In alternative embodiments, high-sensitivity CMOS or other electronic cameras are used in place of ICCD cameras 1114.

An embodiment is used to provide skin dose totals over multiple sessions of treatment; a particular variation of this embodiment has positioning devices or camera mounts suitable for mounting ICCD cameras 1114 in the same position and angle from treatment session to treatment session such that images are comparable from session to session.

Figure 14:
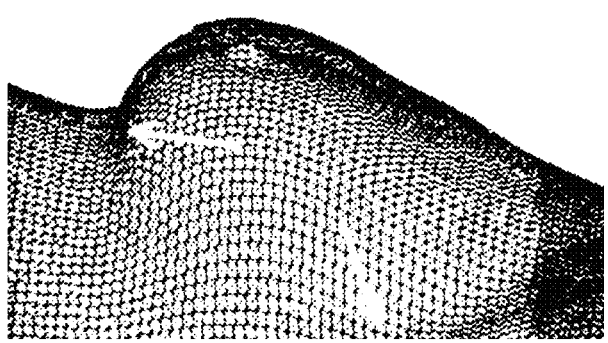
FIG. 14 is an illustration of a three-dimensional model of tissue, such as a breast, derived by stereovision surface extraction and used in mapping image intensity to skin dose.

In operation, as illustrated by the flowchart of FIG. 15, a stereo pair of images under white light is captured 1202 by stereo cameras 1120, and a three-dimensional computer model (FIG. 14), is generated 1204 of skin of breast 1112 of subject 1108 in the area to be treated. In alternative embodiments, the skin is skin of other parts of human or other mammal anatomy, such as skin of a head. A translation or mapping of image intensity at the skin surface in Cherenkov light images, as obtained by one or more ICCD cameras 1114, to surface radiation intensity is determined 1206. The mapping is based in part on ray tracing from skin as modeled in the three dimensional model into the ICCD camera or cameras, and a scale factor determined by calibration. A total session-dose image and model is then cleared 1208.

Once the beam is energized 1210 and treatment begins, a sequence of images of Cherenkov light emitted from skin illuminated by a radiation beam 1130 from accelerator 1102 is obtained 1212 by at least one camera of ICCD cameras 1114 during beam-on intervals while ambient illumination is blanked as previously described. Each image is then processed by applying 1214 the mapping of image intensity in Cherenkov light images as obtained by the ICCD cameras 1114 to surface radiation intensity. The mapped surface intensity is then summed into the session total skin dose 1216 image or model. The mapped surface intensity, the session total skin dose image, and a multisession total skin dose image obtained by summing a current session total skin dose image with prior session skin dose images, are provided 1218 in real time on display 1132. In an alternative embodiment, the Cherenkov light images are summed, then the mapping of image intensity to surface radiation intensity is applied to provide a session total skin dose image. At the end of the session, the session total skin dose and multisession total skin dose are stored over a network 1134 in the subject's electronic health record (not shown), and the session total skin dose is summed into a multisession total skin dose.

The system permits direct observation of the effect altered multileaf collimator 1126 settings, and/or accelerator 1102 rotation about subject 1108, on the areas of skin illuminated by beam 1130. Further, the system permits determination of both session total and treatment total skin dose.

In an embodiment, a pre-treatment simulation of predicted skin radiation dose versus time is copied into memory 1128. During a treatment session, image processor 1124 compares 1219 an image of skin dose derived from surface radiation intensity maps derived from Cherenkov light images to the pre-treatment simulation of skin radiation dose. If the skin dose determined from Cherenkov light images differs by more than a preset, configurable, limit from the pre-treatment simulation, an error 1221 is declared, the beam is turned off, and the session is aborted. This embodiment makes use of the Cherenkov emitted light to prevent subject harm due to overdose, whether from failed equipment or improper system operation.

In an embodiment, the processor 328 is provided with machine-readable instructions in memory 326 for determining if skin and organ dose as administered differs from planned dosage, or from prior dosage, by more than a limit in order to generate an error flag. Such an error flag may be generated if a subject has shed weight, is miss-positioned, or otherwise needs treatment replanning.

In this embodiment, in order to identify differences from prior dosage, during each treatment session a cumulative Cherenkov-light image is stored. During each treatment session other than the first treatment session, processor 328 executed machine readable instructions in memory 326 to retrieve a first or prior Cherenkov image from storage for comparison with current Cherenkov images, and the processor performs edge detection on this first or prior image, and feature extraction on the edge-detected prior image to provide prior features. The processor then performs edge detection and feature extraction on a current Cherenkov image, and the current image features are mapped to prior image features.to determine correspondence points between the images. A displacement between the features of the current image and the prior image is computed, and compared to limits. If the displacement exceeds the limits, the processor then generates an alarm to notify an operator.

In this embodiment, in order to detect differences from plan, a predicted skin-dosage map for dosage of, and simulated cumulative dosage through, a particular treatment session is generated from pre-treatment simulations and saved in memory 326. A do-not-exceed-without-warning dosage is determined and set as a limit in memory 326. A maximum difference percentage is also determined and set as a limit in memory 326. After each fractionated treatment session a totalized skin dosage image for all treatment sessions of this subject is determined, and pixels of the totalized skin dose are compared to the "do not exceed" skin dose and an alarm is provided to a treatment operator if this limit has been exceeded for any pixels. Further, the totalized skin dose is compared to the simulated cumulative skin dose, and if any pixels of the totalized skin dose differ from the simulated skin dose by more than the maximum difference percentage, an alarm is generated. In order to compensate for subject weight loss and precise positioning, the comparison of simulated to totalized dose is performed by processor 328 performing edge detection in simulated skin dose at this treatment stage, performing edge detection in totalized skin dose as determined from Cherenkov radiation, determining a warping of totalized actual skin dose to simulated skin dose, performing image warping, and then comparing totalized actual skin dose to warped simulation skin dose. The images are then compared and if any pixels differ by more than a limit, an alarm is generated.

In an embodiment, in order to compensate for subject weight changes (cancer patients are often ill, have often been subjected to toxic chemotherapies, and may suffer additional effects due to treatment radiation) and minor differences in subject positioning, when totalizing skin dose across sessions, the processor executes machine readable instructions to determine edges and features in both the current image, and in the totalized image. The processor then determines edge offsets between corresponding features and a warping function to correctly superimpose the images. The processor then uses the warping function to warp the current session total image to fit the prior images before adding it to the totalized image in order to compensate for weight loss or subject position.

In another embodiment, the shape of the beam can be readily detected in the Cherenkov image, and if the multileaf collimators or the gantry angle are in error due to computer or human set up error, then the beam delivery can be halted manually (after display of the image to an operator) or automatically in order to avoid erroneous or excessive radiation dose.

In another embodiment, significant biological features of the tissue such as blood vessels, moles and skin variations in absorption appear in the Cherenkov images as variations in detected intensity, and can be used to match the position of the subject each day while administering daily portions of fractionated radiation treatments. Changes in subject position which could occur from day to day can be detected by changes or offsets in locations of these biological features in the images, indicating changes in relative position of beam and subject. These changes may result from subject weight changes, or differences in subject positioning. If these changes are found and exceed limits they can be used to alter the treatment plan or halt therapy until a cause is determined, and changes in subject positioning and/or multileaf collimator settings can be made to compensate.

Figure 16:
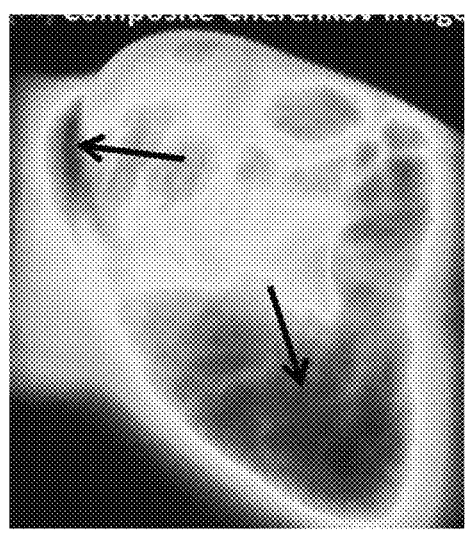
FIG. 16 is an illustration of skin dose intensity as imaged by the system of FIG. 13.

Experiments with a system of the type illustrated in FIG. 13, operated according to the method of FIG. 15, have produced a map of multisession total skin dose as illustrated in FIG. 16, where high total skin dose correlates with areas of maximal skin damage on a human subject, as indicated in photograph FIG. 17. The system has been demonstrated as operable with beam energies of 6 MEV and 10 MEV.

As previously described, internal and surface biological features which absorb radiation and emit Cherenkov and fluorescent light, such as blood in blood vessels and tissue, provide information about the oxygenation of the tissue being treated. Further, images obtained from Cherenkov emissions may be co-registered with prior image data such as the contrast CT scans and MRI scans previously used for simulation and/or planning of treatment. These features provide an internal biological fiducial for treatment verification.

Cherenkov images in visible light, with infrared fluorescent light excluded, may show regions of high and low emission, corresponding to areas of high and low skin dose to a depth of up to a centimeter in tissue.

Correction of Cherenkov Images to Determine Surface Radiation Dose

Cherenkov images of a surface region of subject 102 may be used as a tool to determine surface radiation dose during radiation therapy. However, the signal intensities in raw (as-captured) Cherenkov images are frequently affected by tissue-specific properties that produce artifacts in the Cherenkov images such that the Cherenkov images do not provide an accurate representation of the delivered radiation dose. These tissue-specific features include tissue curvature and heterogeneities in optical properties of the tissue such as tanned skin versus normal skin, moles, tattoos, blood vessels, tumor resection cavities, and optical property changes caused by skin reactions to prior sessions of radiation treatment. In the following, systems and methods are disclosed, which use a reflectance image to correct a Cherenkov image to eliminate or at least reduce artifacts caused by tissue-specific properties so as to generate a corrected Cherenkov image that provides an improved determination of surface radiation dose.

Each of the systems and methods disclosed in FIGS. 2-13 and 15 may be extended to implement the correction methods and/or systems discussed in the following.

Figure 18:
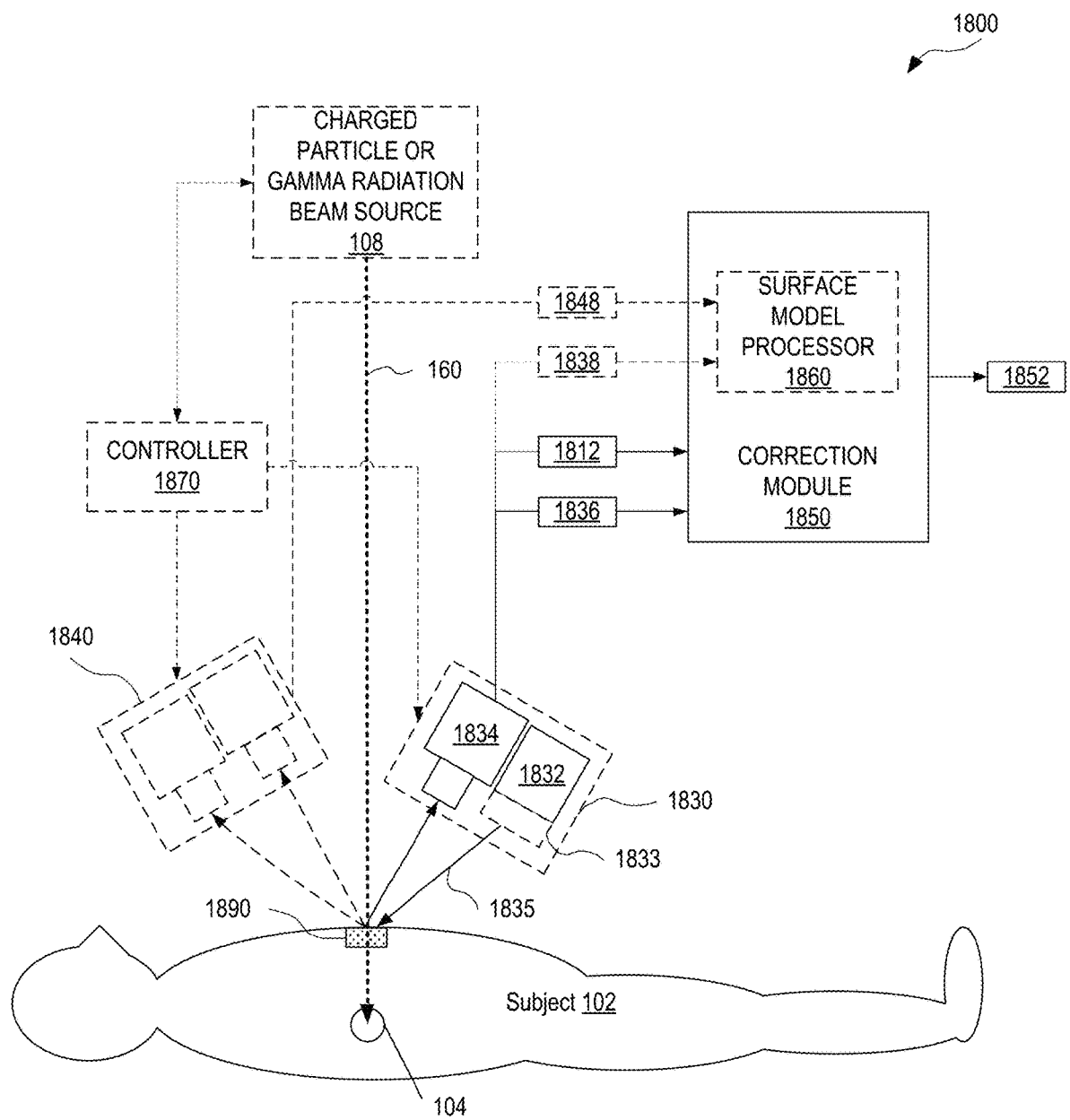
FIG. 18 illustrates one Cherenkov imaging system for determining radiation dose for a surface region of a subject undergoing radiation therapy, according to an embodiment.

FIG. 18 illustrates one exemplary Cherenkov imaging system 1800 for determining radiation dose for a surface region 1890 of subject 102 undergoing radiation therapy. Radiation beam 160, generated by charged particle or gamma radiation beam source 108, is aimed at tumor 104 and generates Cherenkov radiation in the tissue of subject 102. Cherenkov radiation from a surface region 1890, located at and near the surface of subject 102 exposed to radiation beam 160, is imaged from outside subject 102. Depending on the location of tumor 104 within subject 102, surface region 1890 may or may not include at least a portion of tumor 104.

Cherenkov imaging system 1800 includes a camera system 1830 and a correction module 1850. Camera system 1830 includes an electronic camera 1834 and a light source 1832. Camera 1834 captures a Cherenkov image 1812 of Cherenkov radiation emitted from surface region 1890 when subject 102 is exposed to radiation beam 160. Light source 1832 illuminates surface region 1890 with optical illumination 1835. Camera 1834 captures a reflectance image 1836 of optical illumination 1835 as reflected from surface region 1890 when light source 1832 illuminates surface region 1890 with optical illumination 1835. Correction module 1850 corrects Cherenkov image 1812, based upon reflectance image 1836, to produce a corrected Cherenkov image 1852.

Light source 1832 may be monochromatic, broadband, or multi-colored. Without departing from the scope hereof, light source 1832 may omitted from system 1800 and optical illumination 1835 instead be provided through ambient illumination such as room lights 122.

In one embodiment, optical illumination 1835 generated by light source 1832 is diffuse, for example to reduce or avoid glare in reflectance image 1836. In another embodiment, optical illumination 1835 generated by light source 1832 is polarized and camera 1834 is configured to, at least when capturing reflectance image 1836, filter the polarization of optical illumination 1835 reflected by surface region 1890 to deselect the polarization direction of optical illumination 1835 as generated by light source 1832. In one such example, light source 1832 and camera 1834 are equipped with polarizers that are mutually crossed such that only polarization components orthogonal to the polarization direction of optical illumination 1835, as generated by light source 1832, contribute to reflectance image 1836. The polarizer associated with camera 1834 may be mounted on a filter wheel, or similar device, such that Cherenkov image 1812 in some embodiments is captured by the same camera without use of the polarizer.

Surface region 1890 scatters optical illumination 1835 in a manner similar to scattering of the Cherenkov radiation generated in surface region 1890. Hence, the signal intensities in reflectance image 1836 provide a measure of the tissue-specific properties of surface region 1890. Correction module 1850 utilizes reflectance image 1836 to at least partly correct artifacts caused by the tissue-specific properties of surface region 1890 such that corrected Cherenkov image 1852 is free of, or at least less affected by, these artifacts. Thus, corrected Cherenkov image 1852 provides a determination of surface radiation dose for surface region 1890, which is more accurate than that provided by Cherenkov image 1812.

Since Cherenkov image 1812 and reflectance image 1836 are captured by the same camera 1834, Cherenkov image 1812 and reflectance image 1836 are inherently spatially co-registered. In addition, Cherenkov image 1812 and reflectance image 1836 are subject to the same camera properties. As a result, the correction performed by correction module 1850 may further eliminate or reduce artifacts inherent to camera 1834, such as optical aberrations and fixed-pattern electronic noise.

In an embodiment, camera 1834 is a spectrally-sensitive camera capable of providing spectral data permitting distinction between Cherenkov radiation and optical illumination 1835. Camera 1834 may further be able to distinguish between Cherenkov radiation, optical illumination 1835, and fluorescent light, and in a particular embodiment permitting distinction between oxyhemoglobin and deoxyhemoglobin, as discussed above in reference to FIG. 3. A spectrally-sensitive camera suitable for this application may be implemented as a black and white camera equipped with a filter-changer in front of the camera, or a hyperspectral camera, as discussed above in reference to FIG. 3.

In certain embodiments, system 1800 is configured to generate corrected Cherenkov image 1852 in the form of a three-dimensional (3D) surface map, and correction module 1850 includes a surface model processor 1860 that processes 3D surface models and 3D surface maps. In one such embodiment, camera system 1830 further includes a light-structure encoder 1833 that encodes patterns of light and dark, known as structure, onto optical illumination 1835 emitted by light source 1832 while camera 1834 captures at least one structured-light reflectance image 1838. In this embodiment, surface model processor 1860 uses the at least one structured-light reflectance image 1838 to generate a 3D surface model of surface region 1890. In another such embodiment, system 1800 includes a stereo camera 1840 that captures a stereo image 1848. In this embodiment, surface model processor 1860 processes stereo image 1848 to generate the 3D surface model of surface region 1890, as discussed above in reference to FIGS. 3, 14, and 15, for example. Whether the 3D surface model is based upon stereo image 1848 or the at least one structured light reflectance image 1838, correction module 1850 may map corrected Cherenkov image 1852 onto the 3D surface model to output corrected Cherenkov image 1852 in the form of a 3D surface map. In a particular embodiment, one camera of the stereo camera does double-duty as a Cherenkov-light imaging camera and/or as a reflectance-imaging camera.

In an embodiment, system 1800 further includes a controller 1870 that controls timing of capture of Cherenkov image 1812 and reflectance image 1836, and also, if applicable, stereo image 1848 or the at least one structured reflectance image 1838. In one example, controller 1870 pulses on light source 1832 and triggers capture of reflectance image 1836 by camera 1834 while light source 1832 is on. Controller 1870 may trigger capture of Cherenkov image 1812 with timing as discussed above in reference to FIG. 5, while also ensuring that light source 1832 is off when camera 1834 captures Cherenkov image 1812. In embodiments that include stereo camera 1840, controller 1870 may trigger capture of stereo image 1848 by stereo camera 1640. In embodiments that include light-structure encoder 1833, controller 1870 trigger may configure light-structure encoder 1833 and trigger image capture by camera 1834 such that (a) light-structure encoder 1833, which may be a projection cathode-ray tube, a multimirror display device, a liquid-crystal display device, or a slide projector, encodes structure of one or more sequential patterns onto optical illumination 1835 during capture of the at least one structured reflectance image 1838 and (b) light-structure encoder 1833 does not encode structure onto optical illumination 1835 during capture of reflectance image 1812.

Figure 19:
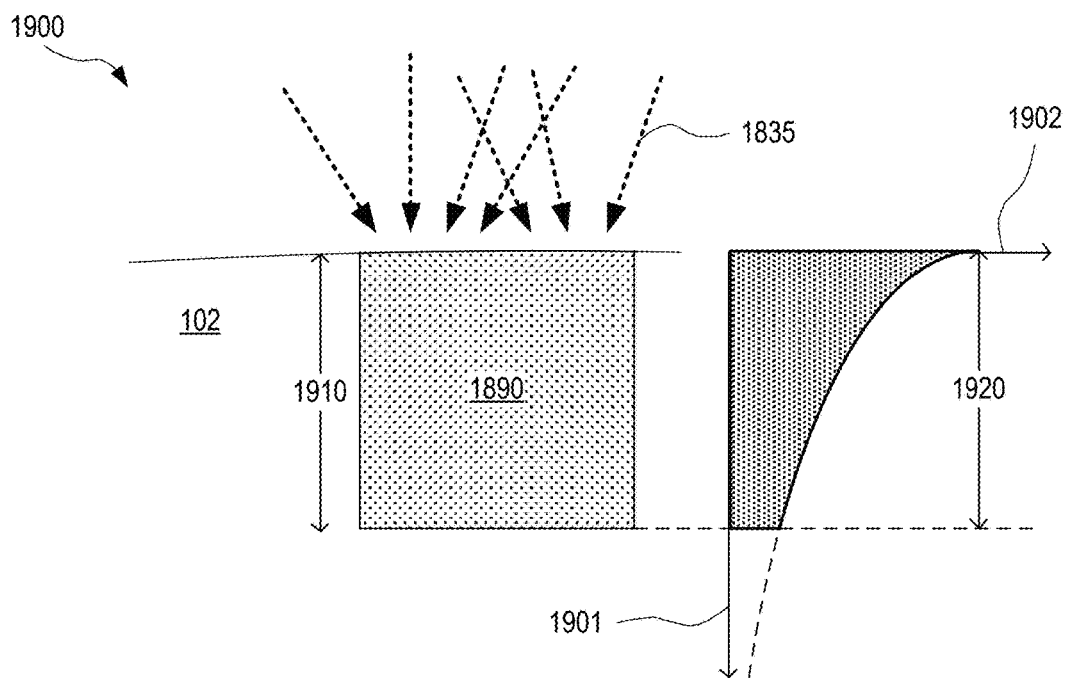
FIG. 19 is a diagram showing exemplary illumination of a surface region of a subject by optical illumination.

FIG. 19 is a diagram 1900 showing exemplary illumination of surface region 1890 by optical illumination 1835 as performed by system 1800. Surface region 1890 is the region of subject 102 from which Cherenkov radiation is captured in Cherenkov image 1812. Surface region 1890 has a characteristic depth 1910 below the surface of subject 102. Typically, characteristic depth 1910 is in the range between two and six millimeters. Surface region 1890 may have shape different from that shown in FIG. 19, without departing from the scope hereof. It is preferred that reflectance image 1836 samples the same region of subject 102 as Cherenkov image 1812. Hence, it is preferred that the penetration depth 1920 of optical illumination 1835 substantially matches characteristic depth 1910. Penetration depth 1920 may refer to the distance 1901 into subject 102, at which the intensity 1902 of optical illumination 1835 has been attenuated to approximately 10%, 30%, or 37% (1/e) of the intensity of optical illumination 1835 at the surface of subject 102. Typically, optical illumination 1835 is in the red to near-infrared spectrum to sample typical values of characteristic depth 1910.

Figure 20:
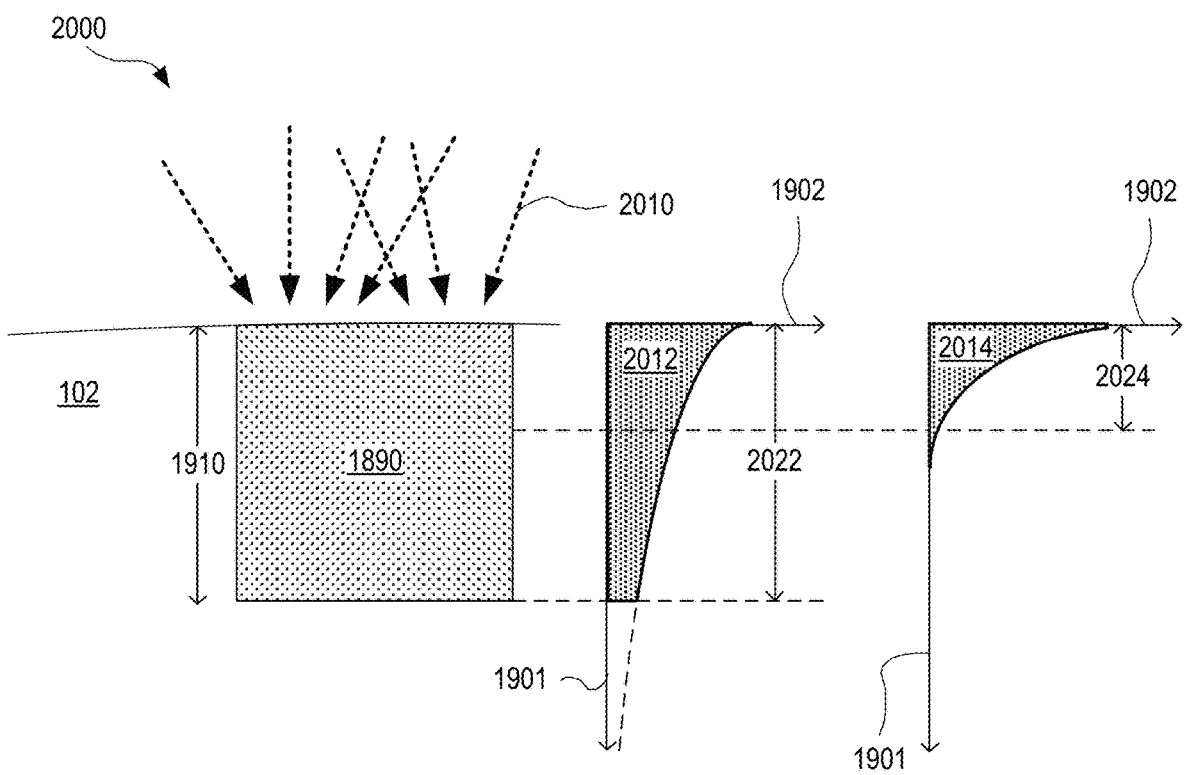
FIG. 20 is a diagram showing exemplary illumination of a surface region of a subject by multi-colored optical illumination.

FIG. 20 is a diagram 2000 showing exemplary illumination of surface region 1890 by multi-colored optical illumination 2010 generated by a multi-colored embodiment of light source 1832. Multi-colored optical illumination 2010 is an example of optical illumination 1835. In the example shown in FIG. 20, multi-colored optical illumination 2010 includes two different spectral components 2012 and 2014. Without departing from the scope hereof, multi-colored optical illumination 2010 may include three or more spectral components. Since Cherenkov radiation is spectrally broadband, multi-colored optical illumination 2010 may be better suited, as compared to monochromatic optical illumination, for sampling surface region 1890 in the same manner as the Cherenkov radiation captured in Cherenkov image 112. Furthermore, multi-colored optical illumination 2010 may be, or include, a spectrally broad component, for example with spectral width of a hundred or hundreds of nanometers. Spectral components 2012 and 2014 have respective penetration depths 2022 and 2024, wherein penetration depth 2022 is different from penetration depth 2024. It is clear from diagram 2000 that spectral components 2012 and 2014, and optionally additional other spectral components, may be combined to better match the sampling intensity profile of Cherenkov radiation from surface region 1890, as compared to the match that may be achieved using only a single spectral component.

Figure 21:
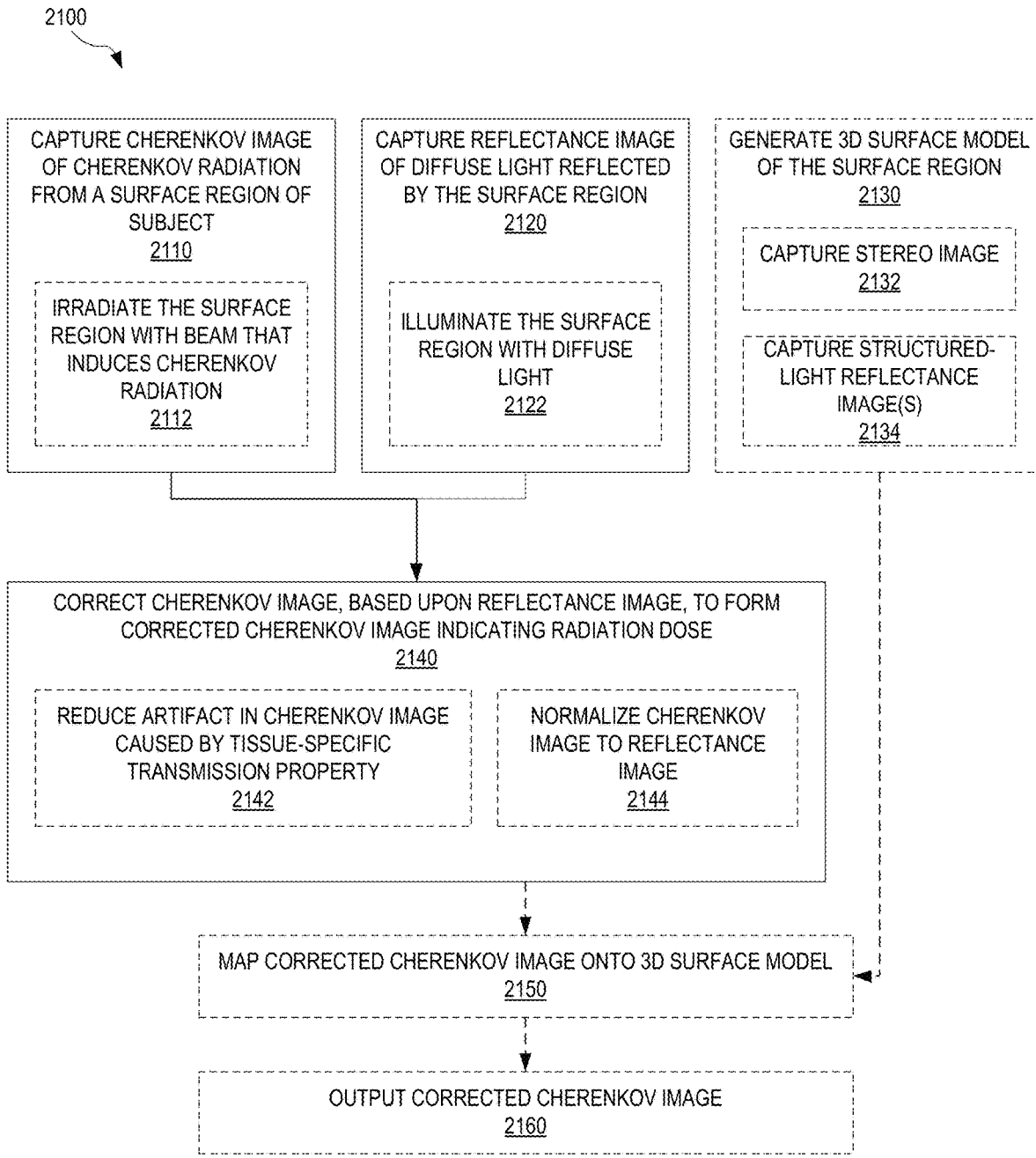
FIG. 21 illustrates one Cherenkov imaging method for determining radiation dose for a surface region of a subject undergoing radiation therapy, according to an embodiment.

FIG. 21 illustrates one exemplary Cherenkov imaging method 2100 for determining radiation dose for surface region 1890 of subject 102 undergoing radiation therapy. Method 2100 is performed, for example, by Cherenkov imaging system 1800.

In a step 2110, method 2100 captures a Cherenkov image of Cherenkov radiation from surface region 1890 of subject 102. In one example of step 2110, camera 1834 captures Cherenkov image 1812. Step 2110 may include a step 2112 of irradiating surface region 1890 with a radiation beam that induces the Cherenkov radiation. In one example of step 2112, charged particle or gamma radiation beam source 108 irradiates surface region 1890 with radiation beam 160.

In a step 2120, method 2100 captures a reflectance image of optical illumination reflected by surface region 1890. In one example of step 2120, camera 1834 captures reflectance image 1836. Step 2120 may include a step 2122 of illuminating surface region 1890 with the optical illumination that produces the reflected light imaged in the reflectance image. In one example of step 2122, light source 1832 illuminates surface region 1890 with optical illumination 1835, such as discussed in reference to FIG. 19 or in reference to FIG. 20. In another example of step 2122, ambient light illuminates surface region 1890 with optical illumination 1835.

In one embodiment, step 2122 illuminates surface region 1890 with diffuse optical illumination. Such diffuse optical illumination may help reduce glare in the reflectance image and also better resemble the sampling of surface region 1890 by the Cherenkov radiation imaged in step 2110.

In another embodiment, step 2122 illuminates surface region 1890 with polarized optical illumination, and step 2120 further includes filtering the reflected optical illumination to produce the reflectance image based upon only randomly polarized reflected light. In one example, step 2120 may image reflected optical illumination only of polarization orthogonal to the polarization of the incident polarized optical illumination. Deselection of the incident polarization ensures that substantially all photons contributing to the reflectance image (or at least the majority of such photons) have undergone a sufficient number of scattering processes within surface region 1890 to be diffusely scattered by surface region 1890, the resulting reflectance image being a scattered-light image with a reduced surface specular reflection component.

In a step 2140, the Cherenkov image captured in step 2110 is corrected, based upon the reflectance image captured in step 2120, to form a corrected Cherenkov image that indicates the radiation dose for surface region 1890, at least with improved accuracy over the Cherenkov image captured in step 2110. In one example of step 2140, correction module 1850 corrects Cherenkov image 1812 based upon reflectance image 1836 to produce corrected Cherenkov image 1852. In an embodiment, step 2140 includes a step 2142 of reducing an artifact in the Cherenkov image captured in step 2110, wherein the artifact is caused by a tissue-specific light-transmission property, as discussed above in reference to FIG. 18. In an embodiment, step 2140 includes a step 2144 of normalizing the Cherenkov image captured in step 2110 to the reflectance image captured in step 2120. In one example of step 2144, correction module 1850 normalizes Cherenkov image 1812 to reflectance image 1836. This example of step 2144 benefits from Cherenkov image 1812 and reflectance image 1836 being spatially co-registered and subject to the same inherent camera properties. In certain embodiments, corrected Cherenkov image 1852 is Cherenkov image 1812 normalized to reflectance image 1836.

Although not shown in FIG. 21, step 2140 may use a model, such as a Monte Carlo simulation, that describes transport of both Cherenkov radiation (and optionally radiation beam 160) and optical illumination within surface region 1890, so as to account for differences in propagation through and sampling of surface region 1890 by the Cherenkov radiation and optical illumination. This model is formed by independently simulating the propagation of each of (a) Cherenkov radiation and (b) the optical illumination for a plurality of different conditions, such as different tissue conditions of subject 101 and different configurations both for the radiation beam that induces the Cherenkov radiation and for the optical illumination. Step 2140 may use modification parameters, according to this model, to compensate for the difference of propagation between the Cherenkov radiation and the optical illumination. The model may be implemented as a looking up database with modification parameters for typical combinations of optical illumination properties (e.g., intensity, beam profile, and spectral composition), radiation beam properties (e.g., beam energy and beam type), geometries (e.g., curvature of surface of subject 101 and incident angles of the radiation beam and the optical illumination). Optionally, the modification parameters for a specific case encountered in real radiation therapy are determined by interpolations within existing modification parameters in the database.

In an optional step 2160, method 2100 outputs the corrected Cherenkov image generated in step 2140. In one example of step 2160, correction module 1850 outputs corrected Cherenkov image 1852.

In certain embodiments, method 2100 includes a step 2150 of mapping the corrected Cherenkov image onto a 3D surface model of surface region 1890. In one example of step 2150, surface model processor 1860 maps corrected Cherenkov image 1852 onto a 3D surface model of surface region 1890 to form a 3D surface radiation dose map. Optionally, such embodiments of method 2100 further include outputting, in step 2160, the corrected Cherenkov image in the form of the 3D surface radiation dose map. These surface model based embodiments of method 2100 may further include a step 2130 of generating the 3D surface model. In one such embodiment, step 2130 includes a step 2132 of capturing a stereo image, which is then processed to generate the 3D model. In another such embodiment, step 2130 includes a step 2134 of capturing at least one structured-light reflectance image, which is then processed to generate the 3D model. In one example of step 2130 implemented with step 2132, stereo camera 1840 captures stereo image 1848, and surface model processor 1860 processes stereo image 1848 to produce the 3D surface model. In one example of step 2130 implemented with step 2134, camera 1834 captures at least one structured-light reflectance image 1838, and surface model processor 1860 processes the at least one structured-light reflectance image 1838 to produce the 3D surface model.

Without departing from the scope hereof, step 2140 may be a stand-alone method, for example suitable for implementation as machine-readable instructions, on non-transitory media, wherein these machine-readable instructions may be executed by a processor to perform step 2140.

Figure 22:
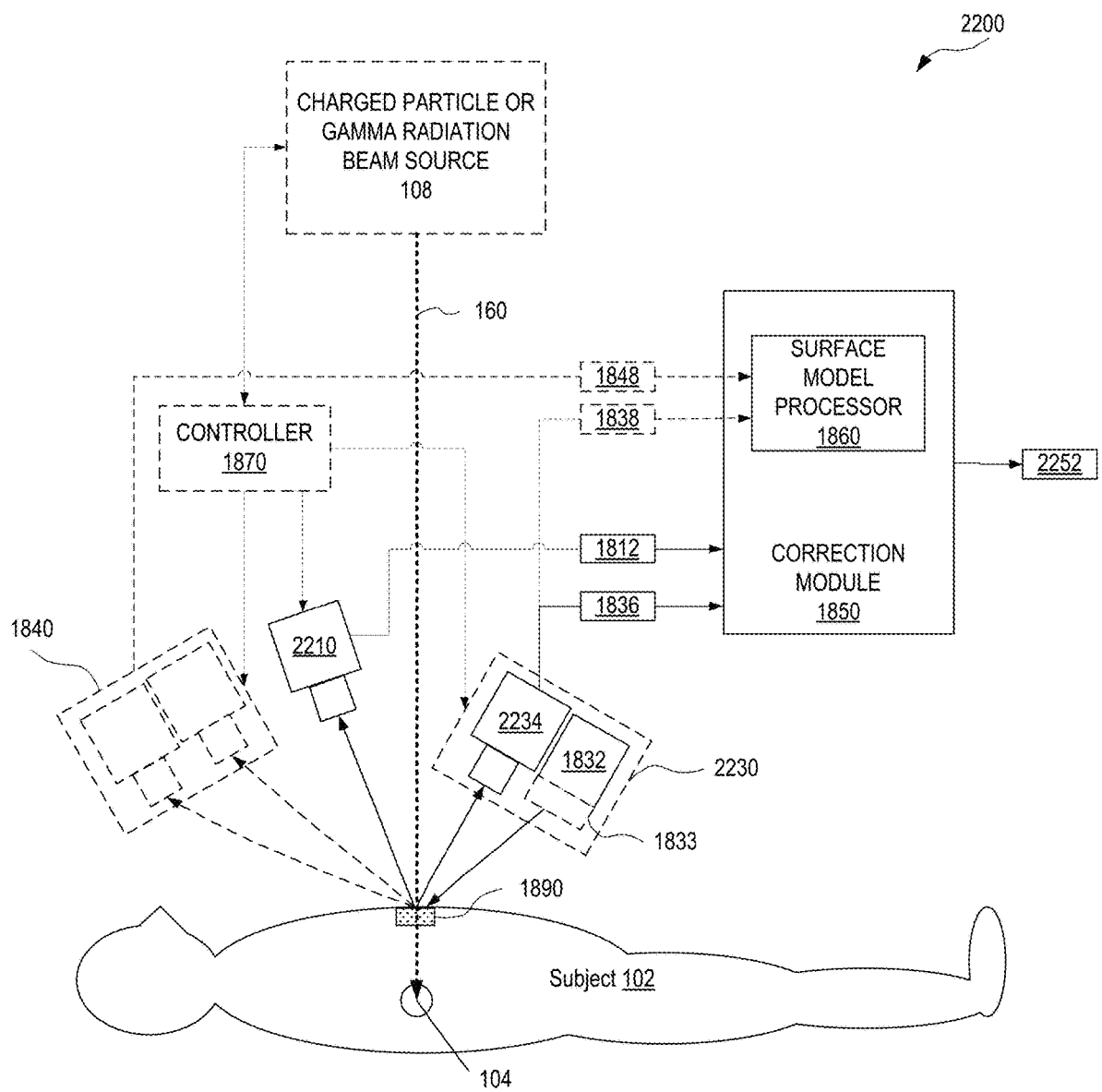
FIG. 22 illustrates another Cherenkov imaging system for determining radiation dose for a surface region of a subject undergoing radiation therapy, according to an embodiment.

FIG. 22 illustrates one exemplary Cherenkov imaging system 2200 for determining radiation dose for a surface region 1890 of subject 102 undergoing radiation therapy. Cherenkov imaging system 2200 is similar to Cherenkov imaging system 1800 except that Cherenkov imaging system 2200 includes two separate cameras 2210 and 2234 that capture Cherenkov image 1812 and reflectance image 1836, respectively. Since Cherenkov imaging system 2200 uses two different cameras, Cherenkov image 1812 and reflectance image 1836 are not spatially co-registered. Therefore, correction module 1850 includes surface model processor 1860. Surface model processor 1860 maps each of Cherenkov image 1812 and reflectance image 1836 onto a 3D surface model of surface region 1890 to generate respective 3D surface maps of Cherenkov image 1812 and reflectance image 1836. Correction module 1850 then corrects the 3D surface map of Cherenkov image 1812 based upon the 3D surface map of reflectance image 1836 to produce a 3D surface radiation dose map 2252. Camera 2234 is implemented with light source 1832 in a camera system 2230. Each of cameras 2210 and 2234 are electronic cameras and may be similar to camera 1834. In addition, controller 1870 (if included) may trigger operation of each of cameras 2210 and 2234. As discussed in reference to FIGS. 18-20, optical illumination 1835 may be monochromatic, multi-colored, or broadband, and light source 1821 may emit optical illumination 1835 as diffuse light or as polarized light. Accordingly, camera 2234 may be equipped with a polarizer that deselects the polarization of polarized optical illumination 1835 to generate images emphasizing scattered light over specular reflected light.

Figure 23:
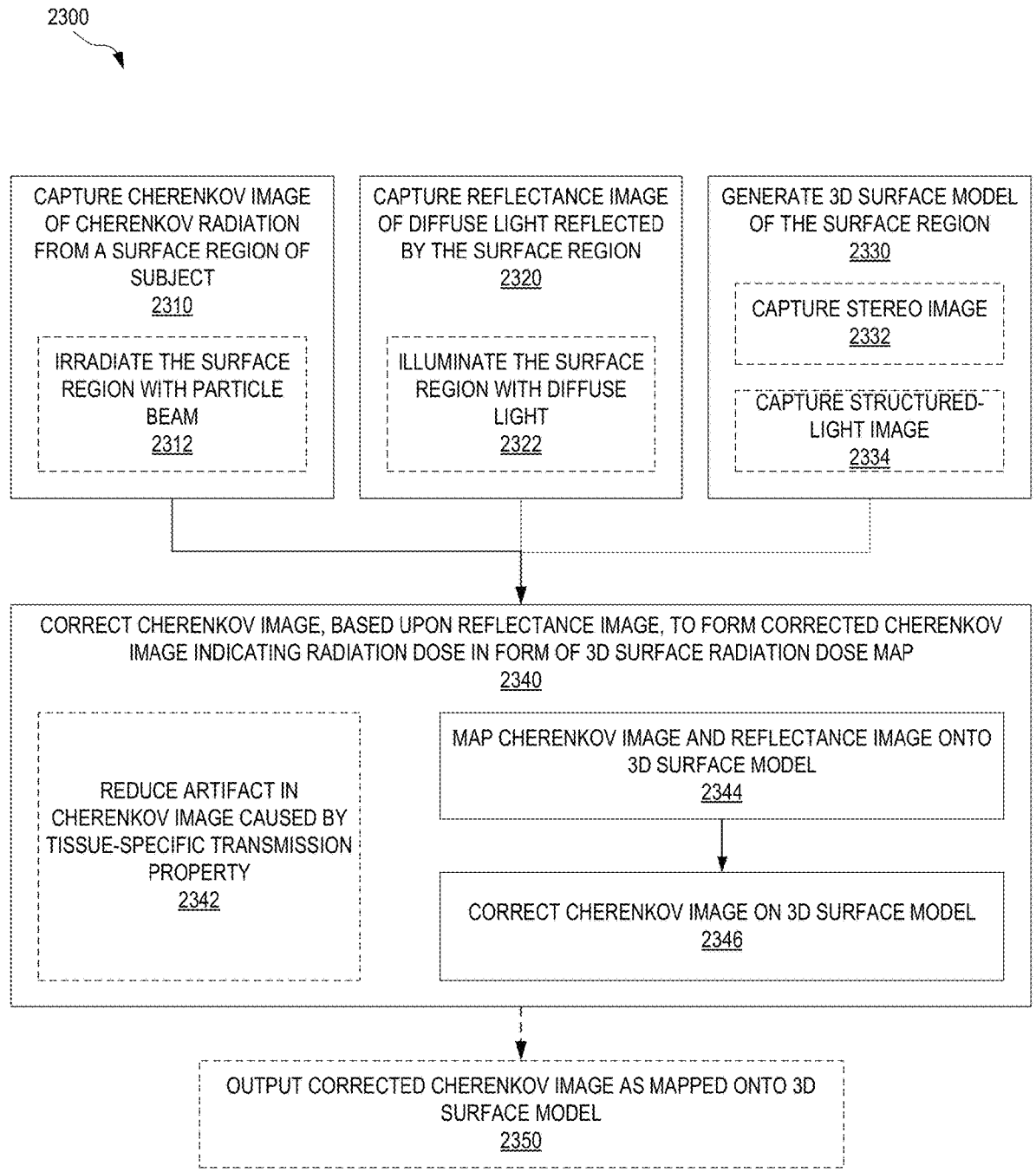
FIG. 23 illustrates another Cherenkov imaging method for determining radiation dose for a surface region of a subject undergoing radiation therapy, according to an embodiment.

FIG. 23 illustrates one exemplary Cherenkov imaging method 2300 for determining radiation dose for surface region 1890 of subject 102 undergoing radiation therapy. Method 2300 is performed, for example, by Cherenkov imaging system 2200.

In a step 2310, method 2300 captures a Cherenkov image of Cherenkov radiation from surface region 1890 of subject 102. In one example of step 2310, camera 2210 captures Cherenkov image 1812. Step 2310 may include a step 2312 of irradiating surface region 1890 with a radiation beam that induces the Cherenkov radiation. In one example of step 2312, charged particle or gamma radiation beam source 108 irradiates surface region 1890 with radiation beam 160.

In a step 2320, method 2300 captures a reflectance image of optical illumination reflected by surface region 1890. In one example of step 2320, camera 2234 captures reflectance image 1836. Step 2320 may include a step 2322 of illuminating surface region 1890 with the optical illumination that produces the reflected light imaged in the reflectance image. In one example of step 2322, light source 1832 illuminates surface region 1890 with optical illumination 1835, such as discussed in reference to FIG. 19 or in reference to FIG. 20. In another example of step 2322, ambient light illuminates surface region 1890 with optical illumination 1835. As discussed above in reference to step 2120 of method 2100, step 2320 may use diffuse or polarized optical illumination.

In a step 2330, method 2300 generates a 3D surface model. In one embodiment, step 2330 includes a step 2332 of capturing a stereo image, which is then processed to generate the 3D model. In another embodiment, step 2330 includes a step 2334 of capturing at least one structured-light reflectance image, which is then processed to generate the 3D model. In one example of step 2330 implemented with step 2332, stereo camera 1840 captures stereo image 1848, and surface model processor 1860 processes stereo image 1848 to produce the 3D surface model. In one example of step 2330 implemented with step 2334, camera 2234 captures at least one structured-light reflectance image 1838, and surface model processor 1860 processes the at least one structured-light reflectance image 1838 to produce the 3D surface model.

In a step 2340, the Cherenkov image captured in step 2310 is corrected, based upon the reflectance image captured in step 2320, to form a corrected Cherenkov image that indicates the radiation dose for surface region 1890, at least with improved accuracy over the Cherenkov image captured in step 2310. Step 2340 forms the corrected Cherenkov image in the form of a 3D surface radiation dose map. In an embodiment, step 2340 includes a step 2342 of reducing an artifact in the Cherenkov image captured in step 2310, wherein the artifact is caused by a tissue-specific light-transmission property, as discussed above in reference to FIG. 18.

Step 2340 includes a step 2344 of (a) mapping the Cherenkov image captured in step 2310 onto the 3D surface model generated in step 2330 to produce a 3D surface map of the Cherenkov radiation, and (b) mapping the Cherenkov image captured in step 2310 onto the 3D surface model generated in step 2330 to produce a 3D surface map of the optical illumination reflected by surface region 1890. In one example of step 2344, surface model processor 1860 maps each of Cherenkov image 1812 and reflectance image 1836 onto the 3D surface model generated in step 2330. Step 2340 further includes a step 2346 of correcting the 3D surface map of the Cherenkov radiation, based upon the 3D surface map of the optical illumination reflected by surface region 1890, to form the 3D surface radiation dose map. In one example of step 2346, correction module 1850 corrects the 3D surface map of the Cherenkov radiation, based upon the 3D surface map of the optical illumination reflected by surface region 1890, to form 3D surface radiation dose map 2252. Step 2345 may include, or consist of, normalizing the 3D surface map of the Cherenkov radiation to the 3D surface map of the optical illumination reflected by surface region 1890.

Although not shown in FIG. 23, step 2340 may use a model, such as a Monte Carlo simulation model, that describes transport of both Cherenkov radiation (and optionally radiation beam 160) and optical illumination within surface region 1890, so as to account for differences in propagation through and sampling of surface region 1890 by the Cherenkov radiation and optical illumination, as discussed in reference to step 2140.

In an optional step 2350, method 2300 outputs the 3D surface radiation dose map generated in step 2340. In one example of step 2350, correction module 1850 outputs 3D surface radiation dose map 2252.

Without departing from the scope hereof, step 2340 may be a stand-alone method, for example suitable for implementation as machine-readable instructions, on non-transitory media, wherein these machine-readable instructions may be executed by a processor to perform step 2340.

In particular embodiments discussed herein with respect to FIGS. 18, 19, 20, 21, 22, and 23, the correction module makes use of a voxel-based light propagation model having scattering parameters and absorbance parameters at each voxel of the model. In these embodiments, the optical parameters extracted by using the optical illumination include the scattering parameter and an absorbance parameter at each voxel of the model. In particular embodiments where the optical illumination is performed at multiple wavelengths, the model may have multiple absorbance parameters at each voxel with each absorbance parameter modeling light absorbance at a particular wavelength of the multiple wavelengths. In embodiments where a three-dimensional model of the subject is determined such as by surface extraction from stereo images, the voxel-based light-propagation model is adjusted to conform to the three-dimensional model by assuming primary absorbance and scattering occurs within the subject. In particular embodiments, the correction module operates by adding a Cherenkov emissions parameter to each voxel of the light propagation model, applying the scattering and absorbance parameters as determined under optical illumination at each voxel of the mode to modeled Cherenkov light, and fitting the Cherenkov emissions parameters to provide a best-fit to observed intensities at pixels of the Cherenkov images.

Each of system 1800, method 2100, system 2200, and method 2300 may be extended to correction of fluorescence images of fluorescence induced by Cherenkov radiation, such as PpIX images discussed above. For example, Cherenkov image 1812 may be replaced by a fluorescence image of Cherenkov-radiation-induced fluorescence, without departing from the scope hereof.

Combinations

The treatment recording and measuring system herein described can be implemented with various combinations of features, some combinations are listed below and some are claimed. These combinations include:

A system designated A for providing and monitoring delivery and accuracy of radiation therapy includes a source of pulsed high energy radiation disposed to provide a radiation beam to a treatment zone, the high energy radiation of at least 0.2 MeV or greater; at least one camera configured to obtain images of Cherenkov light from the treatment zone; and apparatus for adapted to prevent interference by room lighting with the images of Cherenkov light by synchronizing the camera to pulses of the radiation beam, and blanking room lighting during pulses of the radiation beam. The system also has an image processor adapted with machine readable code in a memory to determine an accuracy of actual delivered dose relative to a planned treatment from the images of Cherenkov light.

A system designated AA including the system designated A where the image processor is adapted with machine readable code to estimate cumulative skin dose in the treatment zone from the images of Cherenkov light.

A system designated AB including the system designated A or AA, where the image processor is adapted with machine readable code to resolve patient position relative to the treatment beam from by using vascular and skin structures which appearing in the emitted Cherenkov images as biological alignment features.

A system designated AC including the system designated A, AA, or AB, where a radiation beam extent is determined from the Cherenkov images, and in a system the determined radiation beam extent is used for estimation of accuracy of delivery of the radiation.

A system designated AD including the system designated A, AA, AB, or AC further comprising a positioning device configured to hold the camera in the same angle and position in a first fractionated radiation treatment session and a second fractionated radiation treatment session.

A system designated AE including the system designated A, AA, AB, AC, or AD wherein the memory is configured with machine readable instructions for using a three-dimensional model of a subject to determine a mapping of image intensity in the images of Cherenkov light to the radiation dose deposited in skin of the subject.

A system designated AF including the system designated A, AA, AB, AC, AD, or AE wherein the image processor is configured to acquire multiple images of Cherenkov light during a treatment session.

A system designated AG including the system designated A, AA, AB, AC, AD, AE, or AF, wherein the image processor is configured with machine readable instructions to compare a skin dose determined from pre-treatment simulations to a skin dose determined from imaged Cherenkov light and to interrupt the delivery of radiation if the imaged Cherenkov signal disagrees with the pre-treatment simulations by more than a limit.

A system designated AH including the system designated A, AA, AB, AC, AD, AE, AF, or AG configured with machine readable code to apply the mapping of image intensity from the multiple images of Cherenkov light to determine maps of skin dose, and to determine if changes in position have occurred and to warn an operator if the treatment beam design is providing excessive skin dose or excessive changes in position have occurred.

A system designated AK including the system designated A, AA, AB, AC, AD, AE, AG, or AH wherein the processor is configured with machine readable instructions to indicate on a display when the Cherenkov images show significant differences in the daily images.

A system designated AL including the system designated A, AA, AB, AC, AD, AE, AG, AH, or AK wherein the image processor is configured to sum dosage maps from a first treatment session and a second treatment session to provide a map of total multisession dose.

A method designated B of determining surface dose during radiation treatment of a first object beneath a surface of a second object to limit dose at the surface includes obtaining stereo images of the surface, and extracting a three-dimensional computer model of the surface; determining a mapping of image brightness at the surface in Cherenkov light images obtained by a digital camera to radiation intensity; recording surface brightness at the surface in a plurality of Cherenkov light images; and summing step including using the mapping of image brightness at the surface to translate each Cherenkov light image into a surface dose image, or summing the surface dose images to provide a total session surface dose image; and summing the image brightness in each Cherenkov light image into a total session surface Cherenkov light image and using the mapping of image brightness at the surface to translate the total session surface Cherenkov light image into a total session surface dose image. The method concludes with displaying the total session surface dose image.

A method designated BA including the method designated B and further including summing the total session surface dose image with at least one prior session surface dose image to provide a total treatment surface dose image; and displaying the total treatment surface dose image.

A method designated BB including the method designated B or BA and further including blanking room lighting during acquisition of the Cherenkov light images.

A method designated BC including the method designated B, BA, or BB wherein the second object is a subject and the first object is a tumor.

A method designated BD including the method designated B, BA, BB, or BC and further comprising using an image selected from the group consisting of the total session surface dose image and the total treatment surface dose image to modify a radiation treatment plan for at least one radiation treatment session.

A system designated C for providing and monitoring delivery and accuracy of radiation therapy includes a source of pulsed high energy radiation disposed to provide a radiation beam to a treatment zone, with high energy radiation of at least 0.2 MeV; at least one imaging system configured to obtain observations of light emitted from the treatment zone, the imaging system selected from the group consisting of cameras disposed to image the treatment zone, and photodetectors coupled through optical fibers to gather and detect light from the treatment zone; apparatus adapted to minimize interference by room lighting with the observations; and apparatus adapted to record the observations; wherein the imaging system is synchronized to pulses of the pulsed high energy radiation.

A system designated CA including the system designated C wherein the imaging system comprises at least one camera, and the observations of light are images, and the system further comprises an image processor.

A system designated CB including the system designated CA or C wherein the apparatus adapted to prevent interference by room lighting with the imaging system comprises apparatus adapted to synchronize pulsed room lighting to allow image capture without ambient lighting.

A system designated CC including the system designated C, or CA, wherein the apparatus adapted to prevent interference by room lighting operates through the image processor being adapted with machine readable instructions configured to obtain a first image of the treatment zone during a pulse of the high energy radiation source, and a second image of the treatment zone at a time other than during a pulse of the high energy radiation source; and with machine readable instructions configured to subtract the second image from the first image to provide an image of Cherenkov emissions from the treatment zone.

A system designated CCA including the system designated C, or CA, wherein the apparatus adapted to prevent interference by room lighting operates through a method comprising providing narrowband room lighting at a first wavelength, and wherein images of Cherenkov light exclude light at the first wavelength.

A system designated CD including the system designated CA, CB, or CC wherein the image processor is adapted with machine readable code to estimate a beam shape from the images of Cherenkov light.

A system designated CE including the system designated CD wherein the image processor is adapted with machine readable code to estimate a radiation dose map of the high energy radiation beam on a subject's skin from the images.

A system designated CF including the system designated CA, CB, CC, CCA, CD or CE, where the image processor is further adapted with machine readable code to resolve patient position relative to the treatment beam by using vascular and skin structures appearing in the emitted Cherenkov images as biological alignment features.

A system designated CG including the system designated CA, CB, CC, CCA, CD, CE, or CF where the image processor is further adapted with machine readable code to compare intensity patterns from the images with images from at least one prior treatment session to determine if changes have occurred between sessions.

A system designated CH including the system designated CA, CB, CC, CCA, CD, CE, CF, or CG 10 wherein the image processor is adapted with machine readable code to estimate a radiation dose map of the high energy radiation beam on a subject's skin from the images for a treatment session.

A system designated CI including the system designated CA, CB, CC, CCA, CD, CE, CF, or CG wherein the image processor is adapted with machine readable code to estimate cumulative skin dose across a plurality of a treatment sessions in the treatment zone.

A system designated CK including the system designated CA, CB, CC, CCA, CD, CE, CF, CG, CH, or CI wherein the image processor is configured with machine readable code adapted to using a three-dimensional model of a subject to determine a mapping of image intensity in the images of Cherenkov light to the radiation dose deposited in skin of the subject.

A system designated CL including the system designated CA, CB, CC, CCA, CD, CE, CF, CG, CH, CI, or CK further comprising a positioning device configured to hold the camera in a same location, angle and position in a first fractionated radiation treatment session and all subsequent fractionated radiation treatment session.

A system designated CM including the system designated CA, CB, CC, CCA, CD, CE, CF, CG, CH, CI, CK, or CL wherein the image processor is configured to acquire multiple images of Cherenkov light during a treatment session.

A system designated CN, including the system designated CM, wherein the image data is used to verify delivery as planned by comparison to the prescribed radiation dose.

A system designated CO including the system designated CA, CB, CC, CCA, CD, CE, CF, CG, CH, CI, CK, CL, or CN wherein the image processor is configured with machine readable instructions to compare a skin dose determined from pre-treatment simulations to a skin dose determined from imaged Cherenkov light and to interrupt the delivery of radiation if the imaged Cherenkov signal disagrees with the pre-treatment simulations by more than a limit.

A system designated CP including the system designated C, CA, CB, CC, CCA, CD, CE, CF, CG, CH, CI, CK, CL, CN, or CO wherein the imaging system is spectrally selective such that the imaging system is adapted to capture Cherenkov-stimulated light emissions from tissue and to distinguish this light from Cherenkov light.

A method designated D of determining surface dose during radiation treatment of a first object beneath a surface of a second object to limit dose at the surface includes obtaining at least two images of the surface, and extracting a three-dimensional computer model of the surface therefrom; determining a mapping of image brightness at the surface in Cherenkov light images obtained by a digital camera to radiation intensity; recording surface brightness at the surface in a plurality of Cherenkov light images; and a summing step of either using the mapping of image brightness at the surface to translate each Cherenkov light image into a surface dose image and summing the surface dose images to provide a total session surface dose image, or summing the image brightness in each Cherenkov light image into a total session surface Cherenkov light image and using the mapping of image brightness at the surface to translate the total session surface Cherenkov light image into a total session surface dose image; and displaying the total session surface dose image.

A method designated E of determining surface dose during radiation treatment from imaging of a fractionated radiation therapy includes obtaining multiple images of a surface, and extracting a three-dimensional computer model of the surface therefrom; synchronizing imaging to beam pulses, and obtaining Cherenkov light images; determining a mapping of image brightness at the surface in Cherenkov light images obtained by a digital camera to radiation intensity; recording surface brightness at the surface in a plurality of Cherenkov light images; a summing step selected from the group of using the mapping of image brightness at the surface to translate each Cherenkov light image into a surface dose image and summing the surface dose images, or summing the image brightness in each Cherenkov light image into a total session surface Cherenkov light image, and using the mapping of image brightness at the surface to translate the total session surface Cherenkov light image into a total session surface dose image; and displaying the total session surface dose image.

A method designated EA including the method designated D or E and further including blanking room lighting during acquisition of the Cherenkov light images.

A method designated EB including the method designated D or E further including correcting Cherenkov light images for ambient light by subtracting an ambient light image from an image obtained during a pulse of the beam.

A method designated EC including the method designated D, E, EA, or EB and further including summing the total session surface dose image with at least one prior session surface dose image to provide a total treatment surface dose image; and displaying the total treatment surface dose image.

A method designated ED including the method designated D, E, EA, EB, or EC wherein the surface is normal tissue and a deeper region is a tumor.

A method designated EE including the method designated D, E, EA, EB, EC, or ED wherein the radiation treatment is a fractionated radiation treatment and further comprising using an image selected from the group consisting of the total session surface dose image and the total treatment surface dose image to modify a radiation treatment plan for at least one radiation treatment session.

A Cherenkov imaging system designated F for determining surface radiation dose for a subject undergoing radiation therapy, comprising: a camera system comprising at least one digital camera, the camera system adapted to capture a Cherenkov image of Cherenkov radiation from a surface region of the subject undergoing Cherenkov-radiation-inducing radiation therapy, and to capture a reflectance image of reflectance of optical illumination off the surface region; a light source adapted to generate the optical illumination, and a correction module for correcting the Cherenkov image based upon the reflectance image to form a corrected Cherenkov image that indicates radiation dose for the surface region.

A Cherenkov imaging system designated FA including the Cherenkov imaging system designated F, further comprising a controller for controlling (a) timing of image capture by the first camera to capture the Cherenkov image to minimize room light interference and (b) timing of image capture by the second camera to capture the reflectance image when the surface region is exposed to the optical illumination.

A Cherenkov imaging system designated FB including the Cherenkov imaging system designated F or FA, the light source being configured to generate the optical illumination as diffuse optical illumination.

A Cherenkov imaging system designated FC including the Cherenkov imaging system designated F, FA, or FB, the light source being configured to generate the optical illumination as polarized optical illumination, the camera system including a filter for deselecting a polarization component of the polarized optical illumination to ensure that substantially all photons contributing to the reflectance image have been diffusely scattered by the surface region.

A Cherenkov imaging system designated FC including the Cherenkov imaging system designated F, FA, or FB, the optical illumination having wavelength such that penetration depth of the optical illumination into the subject substantially matches maximum depth of the Cherenkov radiation imaged by the first imaging module.

A Cherenkov imaging system designated FD including the Cherenkov imaging system designated F, FA, FB, or FC, the optical illumination having wavelength such that the penetration depth is between two and six millimeters.

A Cherenkov imaging system designated FE including the Cherenkov imaging system designated F, FA, FC, or FD, the light source being a multi-colored light source for generating the optical illumination at a plurality of different wavelengths to sample a respectively plurality of different depths of the subject so as to match depth-sampling properties of the Cherenkov radiation.

A Cherenkov imaging system designated FF including the Cherenkov imaging system designated FE, the reflectance image being a composite image based upon a plurality of wavelength-specific reflectance images, the Cherenkov imaging system further comprising: a controller for controlling the second camera to capture a plurality of wavelength-specific reflectance images using the plurality of different wavelengths, respectively.

A Cherenkov imaging system designated FG including the Cherenkov imaging system designated F, wherein the camera system is adapted to use a single camera for capturing the Cherenkov image and the reflectance image.

A Cherenkov imaging system designated FH including the Cherenkov imaging system designated F, FA, FC, or FD, the correction module being configured to generate the corrected Cherenkov image by normalizing the Cherenkov image to the reflectance image.

A Cherenkov imaging system designated FJ including the Cherenkov imaging system designated F, FA, FC, FD, or FE wherein the camera system is further adapted to capture a stereo image of the surface region under optical illumination, and further comprising a surface model processor adapted to (a) process the stereo image to produce a three-dimensional surface model of the surface region and (b) map the corrected Cherenkov image onto the three-dimensional surface model to generate a three-dimensional surface radiation dose map.

A Cherenkov imaging system designated FK including the Cherenkov imaging system designated F, FA, FC, FD, FE, or FH further comprising: a light-structure encoder for encoding structure onto the optical illumination to produce structured light to be used by the camera system to capture at least one structured-light reflectance image; and a surface model processor adapted to (a) process the at least one structured-light reflectance image to produce a three-dimensional surface model of the surface region and (b) map the corrected Cherenkov image onto the three-dimensional surface model to generate a three-dimensional surface radiation dose map.

A Cherenkov imaging system designated FL including the Cherenkov imaging system designated F, FA, FC, FD, FE, or FH, the correction module being configured to generate the corrected Cherenkov image in form of a three-dimensional surface radiation dose map by correcting a three-dimensional surface map of the Cherenkov radiation based upon a three-dimensional surface map of the reflectance of the optical illumination; the camera system being further configured to capture a stereo image of the surface region; and further comprising: a surface model processor for (a) processing the stereo image to produce a three-dimensional surface model of the surface region, (b) mapping the Cherenkov image onto the three-dimensional surface model to generate the three-dimensional surface map of the Cherenkov radiation, and (c) mapping the reflectance image onto the three-dimensional surface model to generate the three-dimensional surface map of the reflectance of the optical illumination.

A Cherenkov imaging system designated FM including the Cherenkov imaging system designated F, FA, FB, FC, FD, FE, or FH, the correction module being configured to further take into account discrepancies between light transport properties of the Cherenkov radiation and the optical illumination within the subject when correcting the Cherenkov image.

A Cherenkov imaging system designated FN including the Cherenkov imaging system designated F, FA, FB, FC, FD, FE, FG, FH, FJ, FK, FL, or FM, wherein, the correction module is configured to use a voxel-based light propagation model having scattering parameters and absorbance parameters at each voxel of the model; the optical parameters extracted by using the optical illumination including the scattering parameter and an absorbance parameter at each voxel of the model.

A Cherenkov imaging system designated FO including versions of the Cherenkov imaging system designated FN where the optical illumination is performed at multiple wavelengths, the voxel-based light propagation model having multiple absorbance parameters at each voxel with each absorbance parameter modeling light absorbance at a particular wavelength of the multiple wavelengths.

A Cherenkov imaging system designated FP including versions of the Cherenkov imaging system designated FN or FO wherein the correction module operates by adding a Cherenkov emissions parameter to each voxel of the light propagation model, applying the scattering and absorbance parameters as determined under optical illumination at each voxel of the mode to modeled Cherenkov light, and fitting the Cherenkov emissions parameters to provide a best-fit to observed intensities at pixels of the Cherenkov images.

A Cherenkov imaging method designated G for determining surface radiation dose for a subject undergoing radiation therapy, comprising: correcting a Cherenkov image, the Cherenkov image being an image of Cherenkov radiation emitted from a surface region of the subject undergoing Cherenkov-radiation-inducing radiation therapy, the correcting comprising using a reflectance image, the reflectance image being an image of optical illumination reflected by the surface region, to form a corrected Cherenkov image that indicates radiation dose for the surface region.

A Cherenkov imaging method designated GA including the Cherenkov imaging method designated G, the step of correcting comprising reducing artifact in the Cherenkov image caused by tissue-specific light transmission properties.

A Cherenkov imaging method designated GB including the Cherenkov imaging method designated G or GA, further comprising: capturing the Cherenkov image; illuminating the surface region with the optical illumination; and capturing the reflectance image.

A Cherenkov imaging method designated GC including the Cherenkov imaging method designated G, GA, or GB, in the step of illuminating, the optical illumination being diffuse.

A Cherenkov imaging method designated GD including the Cherenkov imaging method designated G, GA, GB, or GC wherein: in the step of illuminating, illuminating the surface region is done with polarized illumination; and in the step of capturing the reflectance image, a polarization component of the polarized illumination is deselected in the camera system to ensure that substantially all photons contributing to the reflectance image have been diffusely scattered by the surface region.

A Cherenkov imaging method designated GE including the Cherenkov imaging method designated G, GA, GB, GC, or GD further comprising irradiating the surface region with a beam that induces the Cherenkov radiation.

A Cherenkov imaging method designated GF including the Cherenkov imaging method designated G, GA, GB, GC, GD, or GE comprising: in the step of capturing the reflectance image, capturing the reflectance image using same camera as used to capture the Cherenkov image in the step of capturing the Cherenkov image, such that the reflectance image and the Cherenkov image are spatially co-registered; and in the step of correcting, normalizing the Cherenkov image to the reflectance image.

A Cherenkov imaging method designated GG including the Cherenkov imaging method designated G, GA, GB, GC, GD, GE, or GF further comprising: generating a three-dimensional surface model of the surface region; and in the step of correcting: (a) mapping the Cherenkov image onto the three-dimensional surface model to produce a three-dimensional surface map of the Cherenkov radiation, (b) mapping the reflectance image onto the three-dimensional surface model to produce a three-dimensional surface map of the reflectance, and (c) generating the corrected Cherenkov image in form of a three-dimensional surface radiation dose map by correcting the three-dimensional surface map of the Cherenkov radiation based upon the three-dimensional surface map of the reflectance of the optical illumination.

A Cherenkov imaging method designated GH including the Cherenkov imaging method designated G, GA, GB, GC, GD, GE, GF, or GG, the step of generating comprising: capturing a stereo image of the surface region; and processing the stereo image to determine the three-dimensional surface model.

A Cherenkov imaging method designated GJ including the Cherenkov imaging method designated G, GA, GB, GC, GD, GE, GF, GG, or GH the step of generating comprising: capturing a second reflectance image of structured light incident upon the surface region; and processing the second reflectance image to determine the three-dimensional surface model.

A Cherenkov imaging method designated GK including the Cherenkov imaging method designated G, GA, GB, GC, GD, GE, GF, GG, GH or GK further comprising generating the reflectance light image by: (a) illuminating the surface region with the optical illumination, and (b) capturing the reflectance image using a camera; and the step of capturing the second reflectance image comprising: (a) encoding structure onto the optical illumination to produce the structured light, and (b) capturing the second reflectance image using the camera.

A Cherenkov imaging method designated GL including the Cherenkov imaging method designated G, GA, GB, GC, GD, GE, GF, GG, GH or GK, in the step of illuminating, the optical illumination having wavelength such that penetration depth of the optical illumination into the subject substantially matches a maximum depth of the Cherenkov radiation of the Cherenkov image.

The Cherenkov imaging method designated GL, wherein, in the step of illuminating, the optical illumination having wavelength such that the penetration depth is between two and six millimeters.

A Cherenkov imaging method designated GM including the Cherenkov imaging method designated G, GA, GB, GC, GD, GE, GF, GG, GH, GK, GH, or GL, wherein in the step of illuminating, the optical illumination including a plurality of different wavelengths such that the optical illumination samples a respectively plurality of different depths of the subject to match depth-sampling properties of the Cherenkov radiation.

The Cherenkov imaging method designated GM, comprising: in the step of illuminating, illuminating the surface region with optical illumination of a plurality of wavelengths; and in the step of capturing the reflectance image: (a) capturing a respective plurality of wavelength-specific reflectance images, and (b) composing the reflectance image from the plurality of wavelength-specific reflectance images.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A system for providing, and monitoring delivery and accuracy of, a radiation therapy comprising:
    a source of pulsed high energy radiation disposed to provide a radiation beam to a treatment zone, with high energy radiation of at least 0.2 MeV;
    at least one camera configured to obtain images of light emitted from the treatment zone, the cameras disposed to image the treatment zone;
    apparatus adapted to minimize interference by room lighting with the obtained images comprising apparatus adapted to synchronize pulsed room lighting to between pulses of the pulsed high energy radiation to allow obtaining images of Cherenkov light at times without ambient lighting; and
    an image processor;
    wherein the camera is synchronized to obtain the images during pulses of the pulsed high energy radiation;
    wherein the image processor is configured with machine readable code adapted to using a three-dimensional model of a subject to determine a mapping of image intensity in the obtained images of Cherenkov light to a radiation dose deposited in skin of the subject provided by the radiation therapy.

2. The system of claim 1, wherein the image processor is adapted with machine readable code to estimate a beam shape from the obtained images of Cherenkov light.

3. The system of claim 2, wherein the image processor is adapted with machine readable code to estimate the radiation dose of the high energy radiation beam on the subject's skin from the obtained images-of Cherenkov light.

4. The system of claim 2, where the image processor is further adapted with machine readable code to resolve patient position relative to the treatment beam by using vascular and skin structures appearing in the emitted Cherenkov images as biological alignment features.

5. The system of claim 2 where the image processor is further adapted with machine readable code to extract a shape of the beam, and code adapted to compare intensity patterns from the images with images from at least one prior treatment session to determine if changes have occurred and thereby to verify daily accuracy in delivery.

6. The system of claim 1, further comprising a positioning device configured to hold the camera in a same location, angle and position in a first fractionated radiation treatment session and all subsequent fractionated radiation treatment sessions.

7. The system of claim 1, wherein the image processor is configured to acquire multiple images of Cherenkov light during a treatment session.

8. The system of claim 7, wherein the image data is used to verify delivery as planned by comparison to a prescribed radiation dose.

9. A system for providing and monitoring delivery and accuracy of radiation therapy comprising:
   a source of pulsed high energy radiation disposed to provide a radiation beam to a treatment zone, with high energy radiation of at least 0.2 MeV;
   at least one camera configured to obtain images of light emitted from the treatment zone, the camera s disposed to image the treatment zone;
   apparatus adapted to minimize interference by room lighting with the obtained images comprising apparatus adapted to synchronize pulsed room lighting to allow image capture of Cherenkov light at times without ambient lighting; and
   an image processor;
   wherein the camera is synchronized to obtain the images during pulses of the pulsed high energy radiation;
   wherein the apparatus adapted to minimize interference by room lighting includes the image processor being adapted with machine readable instructions configured to obtain a first image of the treatment zone during at least one pulse of the high energy radiation source, and a second image of the treatment zone at a time other than during a pulse of the high energy radiation source; and with machine readable instructions configured to subtract the second image from the first image to provide an image of Cherenkov light from the treatment zone, the first and second images of the treatment zone being obtained while the treatment zone is illuminated with room lighting;
   wherein the image processor is adapted with machine readable code to estimate a radiation dose of the high energy radiation beam on a subject's skin from the images.

10. The system of claim 9, wherein the machine readable code to estimate a radiation dose of the high energy radiation beam on the subject's skin from the images uses a three-dimensional model of the subject to determine a mapping of image intensity in the images of Cherenkov light to the radiation dose deposited in skin of the subject.

11. The system of claim 10, wherein the image processor is adapted with machine readable code to estimate cumulative radiation dose deposited in skin across a plurality of a treatment sessions in the treatment zone.

12. The system of claim 9, the image processor further configured with machine readable code to apply the mapping of image intensity from the multiple images of Cherenkov emissions from the treatment zone, the first and second images of the treatment zone being obtained while the treatment zone is illuminated with room lighting to determine maps of radiation dose to skin, and to determine if changes in position have occurred and to warn an operator if the treatment beam design is providing excessive radiation dose to skin or excessive changes in tissue position have occurred between successive sessions of treatment.

13. A system for providing, and monitoring delivery and accuracy of, a radiation therapy comprising:
   a source of pulsed high energy radiation disposed to provide a radiation beam to a treatment zone, with high energy radiation of at least 0.2 MeV;
   at least one camera configured to obtain images of light emitted from the treatment zone, the camera s disposed to image the treatment zone;
   apparatus adapted to minimize interference by room lighting with the obtained images comprising apparatus adapted to synchronize pulsed room lighting to allow image capture of Cherenkov light at times without ambient lighting; and
   an image processor;
   wherein the camera is synchronized to obtain the obtained images during pulses of the pulsed high energy radiation;
   where the image processor is further adapted with machine readable code to resolve patient position relative to the radiation beam by using vascular and skin structures appearing in the obtained images as biological alignment features.

14. The system of claim 13, where the image processor is further adapted with machine readable code to compare intensity patterns from the obtained images with obtained images from at least one prior treatment session to determine if changes have occurred between sessions.

15. The system of claim 14, wherein the image processor is adapted with machine readable code to estimate a cumulative radiation dose to skin across a plurality of a treatment sessions in the treatment zone.

16. The system of claim 15, wherein the image processor is configured with machine readable instructions to compare a skin determined from pre-treatment simulations to the cumulative radiation dose to skin and to interrupt the delivery of radiation if the cumulative radiation dose to skin disagrees with the pre-treatment simulations by more than a limit.

17. A system for providing, and monitoring delivery and accuracy of, a radiation therapy comprising:
   a source of pulsed high energy radiation disposed to provide a radiation beam to a treatment zone, with high energy radiation of at least 0.2 MeV;
   at least one camera configured to obtain images of light emitted from the treatment zone, the camera s disposed to image the treatment zone;
   apparatus adapted to minimize interference by room lighting with the obtained images comprising apparatus adapted to synchronize pulsed room lighting to allow image capture of Cherenkov light at times without ambient lighting; and
   an image processor;
   wherein the camera is synchronized to obtain the images during pulses of the pulsed high energy radiation to form the obtained images;
   wherein the image processor is configured with machine readable instructions to compare a radiation dose to skin determined from pre-treatment simulations to a radiation dose to skin determined from the obtained images of Cherenkov light and to interrupt the delivery of radiation if the radiation dose to skin determined from the obtained images disagrees with the radiation dose to skin determined from pre-treatment simulations by more than a limit.

18. A method of determining surface dose during radiation treatment of a first object beneath a surface of a second object to limit dose at the surface comprising:
   obtaining at least two images of the surface, and extracting a three-dimensional computer model of the surface therefrom;
   determining a mapping of image brightness at the surface in Cherenkov light images obtained by a digital camera to radiation intensity;
   recording surface brightness at the surface in a plurality of Cherenkov light images;
   a summing step selected from the group consisting of:

using the mapping of image brightness at the surface to translate each Cherenkov light image into a surface dose image, and summing the surface dose images to provide a total session surface dose image; and summing the image brightness in each Cherenkov light image into a total session surface Cherenkov light image, and using the mapping of image brightness at the surface to translate the total session surface Cherenkov light image into a total session surface dose image; and displaying the total session surface dose image.

19. The method of claim 18 further comprising blanking room lighting during obtaining of the Cherenkov light images.

20. The method of claim 18 further comprising correcting Cherenkov light images for ambient light by subtracting an ambient light image from an image obtained during a pulse of the beam.

21. The method of claim 20 further comprising:
summing the total session surface dose image with at least one prior session surface dose image to provide a total treatment surface dose image; and
displaying the total treatment surface dose image.

22. The method of claim 18 wherein the surface is normal tissue and a deeper region is a tumor.

23. A method of determining surface dose during radiation treatment from imaging of a fractionated radiation therapy comprising:

obtaining multiple images of a surface, and extracting a three-dimensional computer model of the surface therefrom;

obtaining Cherenkov light images synchronized to beam pulses, the Cherenkov light images obtained during beam pulses;

determining a mapping of image brightness at the surface in Cherenkov light images obtained by a digital camera to radiation intensity;

recording surface brightness at the surface in a plurality of Cherenkov light images;

a summing step selected from the group consisting of:
using the mapping of image brightness at the surface to translate each Cherenkov light image into a surface dose image, and summing the surface dose images to provide a total session surface dose image; and
summing the image brightness in each Cherenkov light image into a total session surface Cherenkov light image, and using the mapping of image brightness at the surface to translate the total session surface Cherenkov light image into a total session surface dose image; and displaying the total session surface dose image.

24. The method of claim 23, wherein the radiation treatment is a fractionated radiation treatment and further comprising using an image selected from the group consisting of the total session surface dose image and the total treatment surface dose image to modify a radiation treatment plan for at least one radiation treatment session.

* * * * *